(12) United States Patent
Gupta et al.

(10) Patent No.: US 11,788,157 B2
(45) Date of Patent: *Oct. 17, 2023

(54) METHODS OF IDENTIFYING PATIENTS AS HAVING AN INCREASED LIKELIHOOD OF HAVING A HUMAN PAPILLOMAVIRUS (HPV)-ASSOCIATED CANCER OR RECURRENCE OF AN HPV-ASSOCIATED CANCER

(71) Applicant: The University of North Carolina at Chapel Hill, Chapel Hill, NC (US)

(72) Inventors: Gaorav Gupta, Chapel Hill, NC (US); Bhishamjit S. Chera, Chapel Hill, NC (US); Sunil Kumar, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/521,196

(22) Filed: Nov. 8, 2021

(65) Prior Publication Data

US 2022/0170120 A1 Jun. 2, 2022

Related U.S. Application Data

(63) Continuation of application No. 16/573,046, filed on Sep. 17, 2019, now Pat. No. 11,168,373.

(60) Provisional application No. 62/732,117, filed on Sep. 17, 2018.

(51) Int. Cl.
| | | |
|---|---|---|
| *C12Q 1/686* | (2018.01) | |
| *C12Q 1/6844* | (2018.01) | |
| *C12Q 1/70* | (2006.01) | |
| *C12Q 1/6888* | (2018.01) | |

(52) U.S. Cl.
CPC ........... *C12Q 1/708* (2013.01); *C12Q 1/6888* (2013.01)

(58) Field of Classification Search
None
See application file for complete search history.

(56) References Cited

U.S. PATENT DOCUMENTS

| | | | |
|---|---|---|---|
| 5,475,610 | A | 12/1995 | Atwood et al. |
| 5,538,871 | A | 7/1996 | Nuovo et al. |
| 5,602,756 | A | 2/1997 | Atwood et al. |
| 5,612,473 | A | 3/1997 | Wu et al. |
| 2015/0211070 | A1 | 1/2015 | Seligson et al. |
| 2015/0038356 | A1 | 2/2015 | Karlin-Neumann |

FOREIGN PATENT DOCUMENTS

| | | |
|---|---|---|
| EP | 1948816 B1 | 12/2011 |
| EP | 2183387 B1 | 2/2014 |
| WO | 2010036352 A1 | 4/2010 |
| WO | 2015/013681 A1 | 1/2015 |
| WO | 2016/054255 A1 | 4/2016 |
| WO | 2016/168844 A1 | 10/2016 |
| WO | 2018031691 A1 | 2/2018 |
| WO | 2018081130 A1 | 5/2018 |
| WO | 2018/137685 A1 | 8/2018 |
| WO | 2019173280 A1 | 9/2019 |

OTHER PUBLICATIONS

Does a Positive Test for HPV Mean You'll Get Cervical Cancer? Downloaded from Internet on Dec. 24, 2022. https://www.verywellhealth.com/does-hpv-mean-ill-get-cervical-cancer-3132986.*

Lun, Fiona M. F., et al., "Noninvasive prenatal diagnosis of monogenic diseases by digital size selection and relative mutation dosage on DNA in maternal plasma," Proceedgs of the National Academy of Sciences, National Academy of Sciences, vol. 105, No. 50 (2008), pp. 19920-19925.

Sikora, A., et al., "Detection of Increased Amounts of Cell-Free Fetal DNA with Short PCR Amplicons," Clinical Chemistry, vol. 56, No. 1 (2010), pp. 136-138.

European Extended Search Report, EP Patent Application No. 19861643.5, dated May 23, 2022 (15 pages).

Ahn et al., Saliva and Plasma Quantitative Polymerase Chain Reaction-Based Detection and Surveillance of Human Papillomavirus-Related Head and Neck Cancer, JAMA Otolaryngol Head Neck Surg. Sep. 2014 ; 140(9): 846-854.

Bodaghi et al., Could Human Papillomaviruses Be Spread through Blood?, Journal of Clinical Microbiology, Nov. 2005, p. 5428-5434.

Beaty et al., Abstract, International Journal of Radiation Oncology, Biology, Physics, p. S112.

Biron et al., Detection of Human Papillomavirus Type 16 in Oropharyngeal Squamous Cell Carcinoma Using Droplet Digital Polymerase Chain Reaction, ddPCR of HPV in Oropharyngeal Cancer, p. 1554-1551, 2016.

Chera, 2018 ASTRO Annual Meeting Late-breaking Abstract Selection, International Journal of Radiation Oncology, Biology, Physics, p. 1-6.

Chera et al., Rapid Clearance Profile of Plasma Circulating Tumor HPV Type 16 DNA during Chemoradiotherapy Correlates with Disease Control in HPV-Associated Oropharyngeal Cancer, Clin Cancer Res, p. 1-10, 2019.

Cao et al., Quantitation of the Human Papillomavirus DNA in the Plasma of Patients with Oropharyngeal Carcinoma, Int J Radiat Oncol Biol Phys.; 82(3), p. 1-17, 2012.

(Continued)

*Primary Examiner* — Nianxiang Zou

(74) *Attorney, Agent, or Firm* — Thomas | Horstemeyer, LLP

(57) ABSTRACT

Disclosed herein are DNA amplification methods for quantifying DNA fragments of a target DNA in a sample by size. This can be used, for example, to detect tumor-derived viral DNA in blood sample and distinguish it from larger viral DNA from non-tumor sources. In particular, disclosed herein are methods of detecting, monitoring or treating a human papilloma virus (HPV)-associated malignancy in a subject that involves detecting a presence or absence of at least one circulating tumor-derived HPV DNA in a sample from the subject. Kits for accomplishing the same are also provided.

12 Claims, 15 Drawing Sheets

Specification includes a Sequence Listing.

(56) References Cited

OTHER PUBLICATIONS

Cocuzza et al., Human papillomavirus DNA detection in plasma and cervical samples of women with a recent history of low grade or precancerous cervical dysplasia, PLOS One, p. 1-11, 2017.
Gupta, Astro Asco, International Journal of Radiation Oncology, Biology, Physics, p. 1310-1311.
Damerla et al., Detection of Early Human Papillomavirus-Associated Cancers by Liquid Biopsy, ASCO, 1-17, 2019.
Lam et al., Sequencing-based counting and size profiling of plasma Epstein-Barr virus DNA enhance population screening of nasopharyngeal carcinoma, PNAS, vol. 115, No. 22, ES115-ES124, 2018.
Moustafa et al., The blood DNA virome in 8,000 humans, PLOS Pathogens, p. 1-20, 2017.
Jeannot et al., Circulating human papillomavirus DNA detected using droplet digital PCR in the serum of patients diagnosed with early stage human papillomavirus-associated invasive carcinoma, J Path: Clin Res; 2:201-209, 2016.
Lee et al., Predicting response to radical (chemo)radiotherapy with circulating HPV DNA in locally advanced head and neck squamous carcinoma, British Journal of Cancer, 117, 876-883, 2017.
International Search Report issued for PCT/US19/51438, dated Nov. 26, 2019.
Miotke et al., High Sensitivity Detection and Quantitation of DNA Copy Number and Single Nucleotide Variants with Single Color Droplet Digital PCR, Anal. Chem. 86, p. 2618-2624, 2014.
Chugh et al., Systemically Circulating Viral and Tumor-Derived MicroRNAs in KSHV-Associated Malignancies, PLOS Pathogens, vol. 9, Issue 7, p. 1-22, 2013.
Lam et al. Sequencing-based counting and size profiling of plasma Epstein-Barr virus DNA enhance population screening of nasopharyngeal carcinoma. P.N.A.S., 115(22): E5115-5124, published online May 14, 2018.
Dahlstrom et al. Circulating Human Papillomavirus DNA as a Marker for Disease Extent and Recurrence Among Patients With Oropharyngeal Cancer. Cancer 2015; 121 :3455-64.
Jeannot et al. Circulating human papillomavirus DNA detected using droplet digital PCR in the serum of patients diagnosed with early stage human papillomavirus-associated invasive carcinoma. J Path: Clin Res Oct. 2016; 2: 201-209.

* cited by examiner

METHODS OF IDENTIFYING PATIENTS AS HAVING AN INCREASED LIKELIHOOD OF HAVING A HUMAN PAPILLOMAVIRUS (HPV)-ASSOCIATED CANCER OR RECURRENCE OF AN HPV-ASSOCIATED CANCER

CROSS-REFERENCE TO RELATED APPLICATIONS

This application is a Continuation application Ser. No. 16/573,046, filed Sep. 17, 2019, which claims benefit of U.S. Provisional Application No. 62/732,117, filed Sep. 17, 2018, which is hereby incorporated herein by reference in its entirety.

SEQUENCE LISTING

This application contains a sequence listing filed in electronic form as an ASCII.txt file entitled "921404-2030 Sequence Listing_ST25" created on Sep. 16, 2019. The content of the sequence listing is incorporated herein in its entirety.

BACKGROUND

The precise quantification of DNA fragments of a particular size range is of broad interest in molecular biology. Current strategies for quantifying DNA fragments of a particular size generally involve the separation of DNA fragments by gel electrophoresis, size-selective hybridization, and/or high throughput sequencing. It is broadly believed that the Polymerase Chain Reaction (PCR) is unable to measure DNA fragments of a particular size range, but rather detects all DNA fragments that are above a specific minimum size, which is defined by the distance between the primers used to amplify a DNA region of interest (Jacky Lam, et al PNAS 2018).

In a particular embodiment, the ability to specifically quantify DNA fragments of a particular size range enables the more accurate detection of specific subset of human cancers. Viruses are known to promote the development of cancers. For example, infection with high-risk strains of Human Papillomavirus (HPV) is associated with cancers of the cervix, head/neck, anus, vulva, or penis. Other examples of viruses associated with cancer development include Hepatitis B Virus (HBV), Hepatitis C Virus (HCV), Human T-Lymphotropic Virus 1 (HTLV1), Epstein-Barr Virus (EBV), Cytomegalovirus (CMV), Human Endogenous Retrovirus type K (HERV-K), Merkel Cell Virus, Human Immunodeficiency Virus (HIV), and Kaposi's Sarcoma Herpes Virus (KSHV). Since circulating tumor DNA (ctDNA) is released by dying cancer cells, these viral nucleic acids are frequently detectable in the blood of patients with the corresponding cancer type.

There is significant interest in assessing if viral nucleic acids in the circulation can be measured for early cancer detection or other clinical objectives. However, there are two major challenges associated with this concept. First, the amount of circulating tumor-derived DNA (ctDNA) in blood plasma or serum is extremely low—often on the order of a few molecules per mL of blood. Second, viral nucleic acids present in the blood are commonly not derived from tumor-associated viruses but from virions shed from non-tumor tissues. This is established by the finding that DNA sequences from many different types of viruses have been identified in the blood of healthy volunteers (Moustafa et al. PLoS Pathog. 2017 Mar. 22; 13(3):e1006292). Given this finding, it is not evident that the detection of viral sequences in the circulation is, on its own, sufficient to conclude that a patient has a cancer associated with that virus, since the detected viral sequence could derive from normal, non-tumor tissues within the patient. Stated differently, any viral sequence detected in a blood sample could be associated merely with the viral infection itself and have no relationship to tumor burden in the host. This major confounding factor poses a major challenge to measuring circulating viral sequences as a specific marker for cancer detection. Given these key challenges, in the absence of clinical data, it is far from obvious that measurements of viral nucleic acids in the circulation will provide sufficient sensitivity, specificity and predictive value to be of clinical benefit for detecting cancers in patients.

As an illustrative example, PCR-based methods have been reported for detecting HPV DNA in the circulation of patients with HPV-associated preneoplasia or cancers, but these methods also detect HPV DNA in the blood of a substantial proportion of patients who do not have a diagnosis of HPV+ cancer (Bodaghi et al. J Clin Microbiol. 2005 November; 43(11):5428-5434; Cocuzza et al. PLoS One. 2017 Nov. 28; 12(11):e0188592; Ferreira et al. Pathol Res Pract. 2017 July; 213(7):759-765; Chen et al. J Med Virol. 2009 October; 81(10):1792-1796). Thus, since the presence of HPV virus in the circulation of a person could be due to infection of normal tissues, its detection does not necessarily indicate that a person has an HPV-associated cancer. Because currently available detection methods are unable to distinguish between tumor-derived HPV DNA and HPV DNA deriving from normal tissue infected with the virus, they lack sufficient specificity to allow early detection of HPV-associated cancers. Consistent with this, prior PCR-based methods for HPV detection have demonstrated a sensitivity of 54% (95% Cl: 32%-74%) to detect patients with HPV-associated cancers, which is insufficient to be clinically useful to distinguish patients who need further evaluation from those who do not need further evaluation (Jensen et al. Clin Otolaryngol. 2018 May 15. doi: 10.1111/coa.13136. [Epub ahead of print]; Higginson et al. Int J Radiat Oncol Biol Phys. 2015 November; 93(3):S78-S-79; Cao et al. Int J Radiat Oncol Biol Phys. 2012 Mar. 1; 82(3):e351-358; Dahlstrom et al. Cancer. 2015 Oct. 1; 121(19):3455-3464).

Even if a method for detecting circulating viral DNA is clinically demonstrated to have a greater signal in patients with clinically diagnosed cancers, relative to patients without diagnosed cancers, it is underscored that this observation is insufficient to establish the utility of the method for the detection of early-stage cancers in patients that are clinically asymptomatic at the time of the blood draw (Hanna et al. Ann Oncol. 2018 Jul. 13. doi: 10.1093/annonc/mdy251; Jeannot et al. J Pathol Clin Res. 2016 Jun. 28; 2(4):201-209; Lee et al. Br J Cancer. 2017 Sep. 5; 117(6):876-883; Cabel et al. Int J Cancer. 2017 Oct. 15; 141(8):1667-1670; Cao et al. Int J Radiat Oncol Biol Phys. 2012 Mar. 1; 82(3):e351-358; Ahn et al. JAMA Otolaryngol Head Neck Surg. 2014 September; 140(9):846-854). For example, the method may only be detecting larger cancers that would be readily diagnosed in patients using standard screening procedures and clinical practice, but be incapable of detecting smaller cancers that are not detected using standard screening procedures and clinical practices.

Most methods described in the prior art have only been evaluated in retrospective cohorts of patients whose clinical status with regards to cancer is known at the time of the blood testing, without longitudinally following the fate of patients over time. In such a context, as above, it is impossible to know or evaluate whether the analytical test performed would have identified patients with a positive test result—at a statistically significantly level above the background signal—prior to the clinical identification of the corresponding virus-associated cancer.

To establish a blood test's ability to detect cancers in patients who do not have clinically detectable tumors at the time of the blood test, patients would need to be followed over time in longitudinal clinical studies to demonstrate that patients that score positively for the blood test go on to develop detectable tumors over time. In some embodiments the disclosed method is practiced in precisely this longitudinal clinical setting, where patients do not have clinically detectable cancers at the time of blood draw.

The disclosed method resolves the challenges described above by providing a method for quantifying and distinguishing tumor-derived viral sequences in blood from non-tumor-derived viral sequences in the blood. As shown in example 1, the disclosed method can be used in laboratory assays that can be performed on blood samples to distinguish between and specifically quantify either tumor-derived or non-tumor derived cell-free viral DNA in the circulation. As shown in the subsequent examples, this embodiment of the disclosed method was applied in several clinical contexts. In a longitudinal clinical study of patients with newly diagnosed HPV-positive oropharyngeal cancers, it was establish that the disclosed method of analyzing blood samples from cancer versus non-cancer patients can result in 95% sensitivity and 100% specificity in identifying patients with virus-associated cancer. In addition, it has been demonstrated that the quantitative measurements of tumor-derived viral DNA obtained from the disclosed method can be used to predict risk and select patient therapies.

As another application, a prospective clinical study of patients who had no evidence of disease, and who were also clinically asymptomatic at the time of blood specimen collection and testing was conducted. By applying the disclosed methods to blood samples taken from patients enrolled in this longitudinal clinical study, it was established that (i) 70% of patients that develop a positive signal for the present blood test method manifest, after months or years, tumors that are detectable with imaging scans, compared to 9% of total patients in the cohort (p<0.0001), and (ii) 0% of patients that exhibit a negative signal for the present blood test develop clinically detected cancers, compared to 9% of patients in the overall cohort that develop such cancers (p=0.0085). These clinical findings establish that application of this embodiment to the analysis of patient blood samples results in a test for cancer detection in patients with a sensitivity of 100%, a specificity of 95%, a positive predictive value of at least 70%, and a negative predictive value of 100%. Given the exceptional sensitivity of the disclosed method, it is possible that patients who currently test positive yet remain cancer-free may ultimately be diagnosed with cancer with longer clinical follow-up. Thus, the upper limit of the test's positive predictive value may ultimately approach 100% with ongoing follow-up of these higher-risk patients.

These clinical observations demonstrate that the application of the disclosed method to detect circulating tumor-derived viral DNA in patient blood samples results in a cancer detection blood test with a high sensitivity and specificity required to identify patients harboring clinically undetected cancers who exhibit no clinical symptoms of their disease at the time of blood specimen collection. While methods of the disclosed methods are applicable for patients with HPV-associated cancers, the disclosed method described here is also applicable to the detection of tumor-derived circulating nucleic acids from other oncoviruses including, for example, HBV, HCV, HTLV1, EBV, CMV, HERV-K, Merkel cell virus, HIV, and KSHV.

SUMMARY

Disclosed herein are DNA amplification methods for quantifying DNA fragments of a target DNA in a sample by size. This can be used, for example, to detect tumor-derived viral DNA in blood sample and distinguish it from larger viral DNA from non-tumor sources. In particular, disclosed herein are methods of detecting, monitoring or treating a human papilloma virus (HPV)-associated malignancy in a subject that involves detecting a presence or absence of at least one circulating tumor-derived HPV DNA of a particular size range in a sample from the subject. Kits for accomplishing the same are also provided.

For example, disclosed herein is a method for quantifying DNA fragments in a sample by size that first involves fractionating DNA fragments from the sample into droplets at a concentration wherein only 0 or 1 DNA fragments are present in each droplet. This is also known as digital PCR. The next step involves amplifying the DNA in each droplet with a combination of primer/probe sets, wherein each primer/probe set is configured to amplify a non-overlapping region of the DNA fragments to produce an amplicon signal. This is followed by the step of detecting in each droplet the number of amplicon signals. In these methods, the number of amplicon signals is an indication of the minimum size and maximum size of the DNA fragment.

In some embodiments, the minimum size of the DNA fragment can be the maximum distance between the primer/probe sets of the detected amplicons. For example, in a droplet where two amplicons are detected, the distance between the 5' end of the forward primer of the first detected amplicon and the 3' end of the reverse primer of the second detected amplicon can represent the minimum size of the DNA fragment, since if it were any shorter, one or both of the primer/probe sets would not have resulted in amplification.

In some embodiments the maximum size can be the maximum distance between the primer/probe sets of the detected amplicons and the primer/probe sets of the adjacent non-overlapping region that was not amplified. For example, in a droplet where only the first amplicon is detected, the distance between the 5' end of the forward primer of the first detected amplicon and the 5' end of the reverse primer of the second detected amplicon can represent the maximum size of the DNA fragment, since if it were any longer, both of the primer/probe sets would have resulted in amplification.

In some embodiments, the non-overlapping regions of the DNA fragments are separated by at least 1, 5, 10, 20, 30, 40, 50 bp to avoid interference during amplification.

As an example, primer/probe sets can be designed for a 250 bp fragment of DNA with first amplicon region of 100bp, a 50 bp gap, and a second amplicon region of 100 bp. Detection of both amplicons is an indication that the DNA fragment is at least 250 bp long. Detection of only the first amplicon is an indication that the DNA fragment is at least 100 bp long but less than 250 bp. This can be done with a series of amplicon regions in order to provide multiple ranges of size discernment.

Methods for DNA fragmentation into droplets for digital PCR are known, and include fractionation into micro-droplets by emulsification. In some embodiments, the DNA is fractionated based on size prior to performing emulsification into micro-droplets. This can be done, for example, to isolate a range of DNA fragments for quantification by size.

The DNA fragments can be amplified using any known method, such as a PCR method or a non-PCR method.

The disclosed methods can be used in a variety of diagnostic, prognostic, or other assays to quantify the ratio of different fragment sizes of a given DNA target. For example, the disclosed methods can be used to detect smaller tumor-derived viral DNA in blood sample and distinguish it from larger viral DNA from non-tumor sources.

A method is therefore disclosed for quantifying tumor-derived cell-free viral DNA in a blood sample that involves first fractionating DNA isolated from the blood sample into droplets at a concentration wherein only 0 or 1 fragments of tumor-derived viral DNA are present in each droplet. The method then involves amplifying the DNA in each droplet with a combination of primer/probe sets, wherein each primer/probe set is configured to amplify a non-overlapping region of the DNA fragments to produce an amplicon signal, wherein the distance between the primer/probe set is configured to produce fewer amplicons (e.g. one amplicon) with smaller tumor-derived viral DNA fragments and more amplicons (e.g. two or more) with larger viral DNA from a non-tumor source. The method then involves detecting in each droplet the number of amplicon signals, wherein the number of amplicon signals is an indication of tumor-derived cell-free viral DNA or non-tumor sources of circulating viral DNA.

The sizes of tumor-derived viral DNA fragments and viral DNA from non-tumor sources are generally known for many oncoviruses. For example, in some embodiments, human papilloma virus (HPV) DNA circulating in the blood approximates the size of the native HPV genome, which is approximately 8600 bp in length. With spontaneous fragmentation, non-tumor sources of viral DNA may be smaller than the full genome, possibly 8000, 7000, 6000, 5000, or 4000 bp in size. In contrast, tumor-derived HPV DNA fragments circulating in blood are more commonly 70, 80, 90, 100, 120, 130, 140, 150, 160, 170 bp in length. Therefore, the disclosed methods can be used to quantify and distinguish these fragments, for example, by designing primer/probe sets that will only produce two amplicons when the DNA fragment is at least 180, 190, 200, 210, 220 bp in length. It is understood that the specific fragment sizes and primer/probe locations can vary and be tailored using routine skill.

Therefore, in some embodiments, the viral DNA is from a virus selected from the group consisting of human papilloma virus (HPV), Hepatitis B Virus (HBV), Hepatitis C Virus (HCV), Human T-Lymphotropic Virus 1 (HTLV1), Epstein-Barr Virus (EBV), Cytomegalovirus (CMV), Human Endogenous Retrovirus type K (HERV-K), Merkel Cell Virus, Human Immunodeficiency Virus (HIV), and Kaposi's Sarcoma Herpes Virus (KSHV). In particular embodiments, the viral DNA is human papilloma virus (HPV) viral DNA.

Therefore, disclosed herein is a method of diagnosing or monitoring HPV-associated cancer or malignancy in a subject, the method involving detecting one or more tumor-derived cell-free HPV viral DNA in a blood sample using the disclosed methods, wherein the presence of a tumor-derived cell-free HPV viral DNA in the sample is indicative that the subject has an HPV-associated cancer.

If HPV-associated cancer is indicated, the method can therefore further involve radiologically imaging the subject to detect an HPV-associated cancer or malignancy, treating the subject with radiation therapy and/or chemotherapy, or a combination thereof.

In some embodiments, the subject has never been diagnosed with or suffered from an HPV-associated malignancy. In other embodiments, the subject has previously undergone treatment for an HPV-associated malignancy.

The disclosed methods can also be used to monitor treatment. Therefore, also disclosed herein is a method of monitoring HPV-associated cancer or malignancy in a subject, that involves quantifying tumor-derived cell-free HPV viral DNA in blood samples collected at two or more time points during treatment of a subject being treated for the HPV-associated malignancy using the disclosed methods. In some of these embodiments, the presence of the tumor-derived cell-free HPV viral DNA in samples collected at later points in time can be indicative that the subject being treated for an HPV-associated cancer or malignancy will have an increased likelihood for recurrence of the HPV-associated malignancy. Likewise, in some of these embodiments, the rapid clearance of or absence of said tumor-derived cell-free HPV viral DNA in samples collected at later points in time can be indicative that the subject being treated for the HPV-associated malignancy will have a decreased likelihood for recurrence the HPV-associated malignancy. In these cases, the method can also further involve treating the subject with a reduction in radiation therapy and/or chemotherapy if the subject exhibits a rapid clearance of or an absence of the tumor-derived cell-free DNA sequences of HPV in samples collected at later points during the course of treatment.

In some embodiments, the HPV-associated cancer or malignancy is a tumor or cancer of the oral cavity, larynx, oropharynx, tonsils, esophagus, respiratory tissue, breast, skin, cervix, vulva, penis and/or anus. For example, in some embodiments, the HPV-associated malignancy is an HPV-associated oropharyngeal squamous cell carcinoma (OP-SCC). In some embodiments, the HPV is selected from the group consisting of: HPV type 18; HPV type 31; HPV type 33; HPV type 35, HPV type 39; HPV type 45; HPV type 51; HPV type 52; HPV type 56; HPV type 58; HPV type 59; and HPV type 68, or any combination thereof.

According to aspects of the disclosed method, longitudinal analysis of tumor-derived virus nucleic acids in the blood with the disclosed method may be utilized for early detection of virus-positive cancers in individuals who do not present any symptoms related to their malignancy or in whom such symptoms have not yet been identified by clinicians. As demonstrated herein, the disclosed method allows previously unachievable levels of sensitivity and specificity for detecting circulating tumor-derived viral nucleic acids that is applicable to patients with HPV+ cancers, as well as patients with cancers associated with any other virus, including, but not limited to, HBV, HCV, HTLV1, HERV-K, EBV, CMV, Merkel Cell Virus, HIV, or KSHV.

In some embodiments, the disclosed methods can be applied to determine the likelihood of initial diagnosis or recurrence of associated cancer comprising detecting the presence or absence of at least one circulating tumor nucleic acid marker for the relevant virus in blood samples collected from a subject at a single time point or longitudinally over time.

In some embodiments, the disclosed methods can be applied for selecting treatments for oropharyngeal squamous cell carcinoma (OPSCC) or other virus-associated cancer comprising detecting the presence or absence of at least one circulating tumor-derived human papilloma virus (HPV) DNA in samples collected prior to starting treatment and/or at various points in time during treatment from a subject diagnosed with OPSCC or being treated for OPSCC, wherein the presence and/or quantity of said circulating tumor-derived HPV DNA in samples collected at later points in time is indicative that the subject being treated for OPSCC will have an increased likelihood for OPSCC recurrence. Alternatively, rapid clearance of or absence of said circulating tumor-derived HPV DNA in samples collected at later points in time is indicative that the subject being treated for OPSCC will have a decreased likelihood for OPSCC recurrence, and treating the subject with a reduction in radiation therapy and/or chemotherapy if the subject exhibits a rapid clearance of or an absence for said circulating tumor nucleic acid marker for HPV at a specific point in time after initiating cancer therapy.

Also disclosed herein is a method of determining a treatment regimen for human papilloma virus (HPV)-associated cancer or malignancy comprising detecting the presence or absence of at least one circulating tumor-derived HPV DNA in samples collected at different points in time during treatment from a subject diagnosed with HPV-associated cancer or being treated for said HPV-associated malignancy, wherein the absence of or the rapid clearance of said circulating tumor-derived HPV DNA in samples collected at later points in time during treatment is indicative that the subject can be treated with a reduction in radiation therapy and/or chemotherapy.

Also disclosed herein is a method of detecting, monitoring and/or treating a human papilloma virus (HPV)-associated malignancy in a subject, the method comprising detecting a presence or absence of at least one circulating tumor-derived HPV DNA in samples collected from the subject at various points in time during a course of treatment, wherein the presence of the circulating tumor-derived HPV DNA in samples collected at later points in time during the course of treatment is indicative that the subject has an HPV-associated malignancy or an increased likelihood for an HPV-associated malignancy recurrence, and the rapid clearance of or absence of circulating tumor-derived HPV DNA in samples collected at later points in time during the course of treatment is indicative that the subject does not have an HPV-associated malignancy or has a decreased likelihood for an HPV-associated malignancy.

Also disclosed herein is a method for monitoring and/or treating a human papilloma virus (HPV)-associated malignancy in a subject comprising detecting levels of a circulating tumor-derived HPV DNA in samples collected at various points in time from the subject diagnosed with or being treated for the HPV-associated malignancy; determining a circulating tumor-derived HPV DNA profile for the subject; and adjusting a treatment regimen for the HPV-associated malignancy according to the circulating tumor-derived HPV DNA profile, wherein a subject with a favorable circulating tumor-derived HPV DNA profile is treated with a de-intensified treatment regimen.

Also disclosed herein are kits including components as described herein for detecting, monitoring and/or treating malignancies in a subject as described herein, and instructions for the use thereof. For example, the kits can contain primer/probe sets configured to amplify a non-overlapping regions of the DNA fragments to produce amplicon signals for detecting HPV viral DNA fragments by minimum and maximum size, and instructions for the use thereof.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A) Dual fragment HPV16 assay to detect tumor viral DNA. Shown are the digital PCR fluorescence detection plots for simultaneous detection of two distinct fragments of the HPV16 genome. Examples are shown for the single positive controls, dual fragment positive control, intact HPV genome control, and two patient plasma DNA samples. Gates used to quantify single- and double-positive droplets are shown, as described in the methods. FIG. 1B) Analysis of 12 plasma DNA samples from patients with HPV+ oropharyngeal cancer using this assay uniformly demonstrates the presence of tumor-derived viral DNA—indicated by abundance of both fragments in single positive droplets and very rare co-occupancy of both targets in the same droplet (in contrast to the intact genome control).

FIG. 3A) Schematic of timepoints when blood was sampled in a cohort of oropharyngeal cancer patients prior to, during, and after receiving chemoradiotherapy (CRT). FIG. 3B) Two patterns of plasma ctHPV16 profile observed after initiating CRT. In some patients (red lines), ctHPVDNA levels are highest pre-treatment and diminish after initiating therapy. In other cases (blue lines), ctHPVDNA levels increase soon after starting treatment, possibly due to a spike in cancer cell death. In all cases, ctHPVDNA levels are markedly reduced at the end of CRT, indicating that ctHPVDNA levels are correlated with the volume of active cancer in patients. FIG. 3C) A subset of patients have rapid clearance kinetics of ctHPVDNA during CRT, with >95% of ctHPVDNA cleared by week 4 of CRT. FIG. 3D) Another subset of patients has delayed kinetics of ctHPVDNA clearance after CRT, which may be correlated with poor or delayed response to CRT.

FIG. 4A) There was a strong correlation between the HPVDNA dPCR assay described in Example 1, when applied to the tumor biopsy specimen, and tumor HPV copy number assessed by NGS. This validates both the HPVDNA assay and NGS using orthogonal assays on the same samples. FIG. 4B) There is a statistically significant correlation between tumor HPV copy number per cellular genome and pre-treatment ctHPVDNA in the blood, normalized to tumor volume ("ctHPVDNA density"). This indicates that the level of ctHPVDNA detected in blood is correlated with HPV copy number in the associated tumor. FIG. 4C) A bioinformatics analysis pipeline was developed to distinguish HPV+ HPV cancers that have evidence of HPV integration into the human genome versus those cancers that have purely episomal HPV, using the tumor NGS data. FIG. 4D) A circos plot is shown demonstrated the observed rearrangements in a cancer with episomal HPV (left) and integrated HPV (right). The example with integrated HPV shown here has an integration site that maps to a region on chromosome 8 (see the dark black lines). FIG. 4E) Higher tumor HPV copy number correlates with a greater likelihood of non-integrated (episomal only) HPV. FIG. 4F) Higher ctHPVDNA levels in blood also correlate with a higher likelihood of non-integrated (episomal only) HPV in the associated cancer. Thus, ctHPVDNA can also provide information on the status of the HPV genome in the associated cancer—i.e., if it is integrated versus episomal.

FIG. 5A) A schematic for stratifying patients based on their ctHPVDNA profile. Patients with abundant pre-treatment ctHPV16DNA that is rapidly cleared (>95% by day 28) are classified as having a favorable ctHPVDNA profile. All other patients are classified as having an unfavorable ctHPVDNA profile. FIG. 5B) Favorable ctHPVDNA profile is observed in ~30% of patients with clinically favorable (<T4 and <=10 pack-year smoking history) and in ~30% of patients with clinically unfavorable (T4 or >10 pack-year smoking history) disease.

FIG. 6A) Proportion of patients in each subgroup who had a positive post-treatment neck dissection (i.e., regionally persistent disease), regional recurrence, and distant metastasis. Patients who had unfavorable clinical risk factors and an unfavorable ctHPVDNA profile had the highest risk of adverse disease events. FIG. 6B) Kaplan-Meier analysis of regional disease (persistent or recurrent) free survival stratified by clinical risk and ctHPVDNA profiles. Patients with a Favorable ctHPV16DNA Profile had 100% regional disease control, regardless of smoking history (5 patients were heavy smokers). In contrast, clinical higher risk patients with an Unfavorable ctHPVDNA Profile had significantly reduced regional disease control. P, two-tailed logrank test for a trend.

DETAILED DESCRIPTION

Figure 1A:
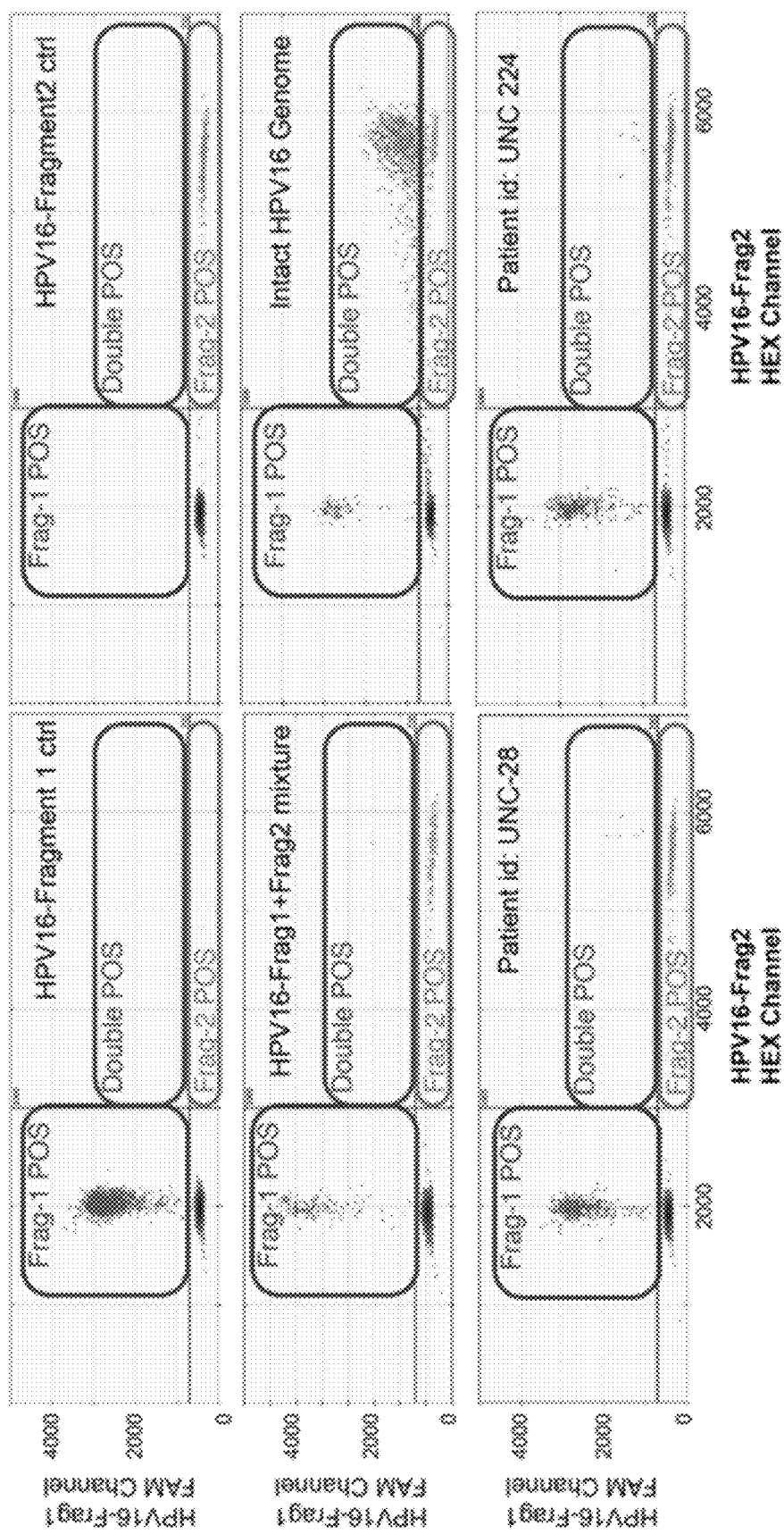
FIGS. 1A and 1B.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

As used herein "human papilloma virus" or "HPV" refers to small, non-enveloped, double-stranded DNA viruses that infect the cutaneous and/or mucosal epithelium. As understood by those skilled in the art, over 100 HPV genotypes are known to exist. Sexually transmitted, mucosotropic HPVs are further subcategorized as high risk (e.g. HPV16 and HPV18) or low risk (HPV6 and HPV11).

As used herein, HPV-associated malignancies include those of the head and neck (larynx, oral cavity, oropharynx, tonsils, and esophagus), respiratory tissue, breast, skin, cervix, vulva, penis and anus. Malignancy and cancer are used interchangeably.

As used herein, "detecting" or "detection" means testing, screening or otherwise determining the presence and/or absence of at least one tumor nucleic acid marker for HPV in a sample. Such detecting or detection can be carried out by methods described herein, including those known in the art as applicable to this technology, for example, nucleic acid amplification, hybridization-based detection, microarray and next generation sequencing.

Also as used herein, the terms "treat," "treating" or "treatment" may refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, delay of the onset of the disease, disorder, or illness, and/or change in clinical parameters of the condition, disorder, disease or illness, etc., as would be well known in the art.

As used herein, the term "monitoring" refers to assessing the therapeutic efficacy of a treatment for patients with a cancer. As used herein, the term "surveillance" refers to the detection of associated malignancy in subjects, who may or may not have a clinically diagnosed or symptomatic cancer.

As used herein, a subject has an "increased likelihood" of some clinical feature or outcome (e.g., recurrence or progression) if the probability of the subject having the feature or outcome exceeds some reference probability or value. The reference probability may be the probability of the feature or outcome across the general relevant subject or patient population. For example, if the probability of recurrence in the general oropharyngeal cancer population is X % and a particular patient has been determined by the methods to have a probability of recurrence of Y %, and if Y>X, then the patient has an "increased likelihood" of recurrence. Alternatively, a threshold or reference value may be determined and a particular patient's probability of recurrence may be compared to that threshold or reference.

As used herein, "sample" refers to a biological sample containing a tumor nucleic acid marker for HPV. The sample may be tissue, cells, or any fluid taken from the human body, e.g., blood, plasma, urine, saliva, etc. In particular embodiments, the sample is a blood-based sample. Accordingly, the sample may be whole blood or components thereof such as serum or plasma.

Also disclosed herein are methods for detection, treatment and surveillance of human papillom associated malignancies and kits for accomplishing the same.

Also disclosed herein are methods for quantifying viral nucleic acids in the circulatory system that are specifically derived from tumors, and for distinguishing these tumor-derived viral nucleic acids from other sources of circulating viral nucleic acids.

Disclosed herein are DNA amplification methods for quantifying DNA fragments of a target DNA in a sample by size. This can be used, for example, to detect tumor-derived viral DNA in blood sample and distinguish it from larger viral DNA from non-tumor sources. In particular, disclosed herein are methods of detecting, monitoring or treating a human papilloma virus (HPV)-associated malignancy in a subject that involves detecting a presence or absence of at least one circulating tumor-derived HPV DNA in a sample from the subject. Kits for accomplishing the same are also provided.

The disclosed method can be performed within thousands of micro-droplets (also referred to herein as droplets) generated through, for example, emulsification and/or water-in-oil droplet partitioning, such as is described in Hindson et al. Anal Chem. 2011 Nov. 15; 83(22):8604-8610, Pinheiro et al. Anal Chem. 2012 Jan. 17; 84(2):1003-1011 and Kanagal-Shamanna. Methods Mol Biol. 2016; 1392:33-42, or any other method known to those versed in the art to separate a sample into discrete and/or volumetrically defined partitions for analysis of tumor derived versus non-tumor derived DNA present in the partitions/sample. In the case of micro-droplets, the size of the droplets can be micro-, nano-, pico-, or femto-scale.

As disclosed herein, the micro-droplets are generated such that they each contain at most a single targeted viral nucleic acid. In embodiments where only two distinct regions of the viral nucleic acid are detected, a micro-droplet containing the targeted viral nucleic acid will be either single-positive, i.e., positive for one of the detection signals, or double-positive, i.e., positive for both of the detection signals. As disclosed herein, the relative numbers of the single-positive and double-positive micro-droplets and double-positive droplets provide quantitative information making it possible to quantitatively determine the relative amounts of tumor-derived and non-tumor derived viral DNA in the sample.

In embodiments where the PCR is used to detect two physically distinct regions, included is a forward and reverse primer pair corresponding to each detected region. In some embodiments, the detection may be performed using digital PCR, droplet digital PCR, emulsion PCR or micro-droplet PCR according to procedures that would be appreciated by one of skill in the art. As disclosed herein, micro-droplets containing tumor-derived circulating viral nucleic acids have fewer positively detected viral nucleic acid regions relative to micro-droplets containing non-tumor-derived circulating viral nucleic acids. In the simplest case where only 2 different regions in the viral nucleic acid are targeted for detection, the disclosed method identifies micro-droplets containing non-tumor-derived circulating viral DNA as those that are positive for both of the detection signals employed for the different targeted regions (double-positive); by contrast, in this simplest case, micro-droplets containing tumor-derived circulating viral nucleic acid are positive for only one detection signal but not both signals simultaneously.

To take an illustrative example, if the target nucleic acid regions for detection comprise fragments of ~70-100 bp, two or more target regions separated by 100 bp would never be present on the same viral DNA molecule if the molecule was derived from circulating tumor DNA. Under this scenario, the simultaneous detection of both target fragments within the same micro-droplet must be due to co-occupancy within the same micro-droplet of two distinct target fragment molecules, each containing one of the regions targeted for detection. Thus, if the analyzed samples contain non tumor-derived viral DNA, there will be a higher frequency of micro-droplets that test positive for two or more target fragments than would be expected based on the frequencies of each target region analyzed individually.

For example, one quantitative measurement of the proportion of non-tumor-derived viral DNA fragments in the sample is [fraction(droplets double-positive for both detection signals)−fraction(droplets positive only for detection signal 1)*fraction(droplets positive only for detection signal 2)]. It follows that the fraction of tumor-derived viral DNA in the sample is [1−[fraction(droplets double-positive for both detection signals)−fraction(droplets positive only for detection signal 1)*fraction(droplets positive only for detection signal 2)]]. The corresponding quantitative measure of tumor-derived viral DNA would be [#(droplets positive only for detection signal 1)+#(droplets positive only for detection signal 2)]*[proportion of tumor-derived viral DNA fragments]=[#(droplets positive only for detection signal 1)+#(droplets positive only for detection signal 2)][1−fraction(droplets positive for both detection signals)+fraction(droplets positive only for detection signal 1)*fraction(droplets positive only for detection signal 2)]. These formulae are provided as illustrative examples of how the raw detection signal data can be converted into measurements of tumor-derived and non-tumor-derived viral DNA in the sample, with the understanding there are other formulae that could be utilized for the same purpose.

The disclosed methods can also be applied in cases where 3 or more regions, each with its own detection signal, are detected in each micro-droplet or other parallelized micro-reaction chamber. In this context, the mathematical formula for quantification of tumor-derived and non-tumor derived viral DNA can be generalized on the basis of the reasoning provided above for 2 amplified regions.

While the examples above considered detected viral DNA regions of size ~70-100 bp separated by at least about 50 bp, about 60 bp, about 70 bp, about 80 bp, about 90 bp or about 100 bp, it should be understood that both the size of the detected DNA fragments and their distance may be varied and are not fixed in relation to the disclosed methods.

Returning to the embodiment in which two different regions are targeted for detection, double-positive micro-droplets may on occasion arise from the co-incidence of two smaller fragments of viral nucleic acid within a single micro-droplet, each fragment containing just a single region targeted for detection, as opposed to the desired measurement of one larger fragment encompassing both of the regions targeted for detection. In some embodiments, this possibility can be ruled out, or the extent to which it is occurring quantified, by comparing the relative frequencies of double-positive and single-positive droplets, and confirming that the frequency of double-positive droplets is approximated by the product of the frequencies of the single-positive droplets, and reduces in prevalence by the square of the dilution factor when re-analyzed at a lower concentration.

In some embodiments, nucleic acids isolated from blood samples are emulsified into micro-droplets such that the vast majority of micro-droplets contain either one or none of the viral nucleic acids that are being targeted for detection. Experimental methods for determining the correct micro-droplet volume and blood sample dilution factors are provided herein. Subsequent to emulsification, nucleic acid detection methods, which may include PCR-based methods, are employed to detect two or more regions of the targeted viral nucleic acid that are physically separated from one another. In some embodiments, each viral region being targeted detection is associated with a unique detection signal, for example a unique fluorescent color.

Also disclosed herein are methods of detecting ctHPVDNA in HPV-OPSCC patients. The methods generally involve detecting the presence of tumor-derived viral DNA using a nucleic acid amplification, such as polymerase chain reaction (PCR), in an emulsified context in which least two distinct regions are amplified to distinguish between tumor-derived viral DNA, which is fragmented, and non-tumor-derived intact virions, whose DNA is not fragmented. Also disclosed herein are nucleic acid probes and nucleic acid primers, as well as kits comprising same, for use in a said method.

Also disclosed herein are methods for identifying the prognosis of individuals with HPV-associated OPSCC that can be successfully treated by de-intensified chemoradiotherapy (CRT), methods for identifying tumor-specific biomarkers that are predictive of HPV-associated OPSCC relapse or recurrence after treatment, and methods of identifying the prognosis of individuals with HPV-associated OPSCC who are at risk for relapse or recurrence after treatment.

Subjects suitable to be treated by the disclosed methods include, but are not limited to mammalian subjects. Mammals include, but are not limited to, canines, felines, bovines, caprines, equines, ovines, porcines, rodents (e.g., rats and mice), lagomorphs, primates, humans and the like, and mammals in utero. Any mammalian subject in need of being treated or desiring treatment is suitable. Human subjects of any gender (for example, male, female or transgender) and at any stage of development (i.e., neonate, infant, juvenile, adolescent, adult, elderly) may be treated. Subjects may be of any race or ethnicity, including, but not limited to, Caucasian, African-American, African, Asian, Hispanic, Indian, etc., and combinations thereof. It should be further noted that subject and patient are used interchangeably.

In particular embodiments, the subject has never been diagnosed with or suffered from associated malignancy. In other embodiments, the subject may be diagnosed with, afflicted with, suffering from or at risk for associated malignancy. In some embodiments, the subject has previously undergone treatment for associated malignancy. In other embodiments, the subject may be in remission from a virus-associated malignancy. In some embodiments, the subject is a smoker. In some embodiments, the subject is a non-smoker.

Detection of ctHPVDNA

Methods for determining the level of biomarker nucleic acid, for example, a ctHPVDNA, such as ctHPV16DNA, in a sample may involve the process of nucleic acid amplification, e.g., by PCR, ligase chain reaction (LCR), transcription-based amplification systems, (TAS) self-sustained sequence replication (3SR), nucleic acid sequence-based amplification (NASBA), strand displacement amplification (SDA) and branched DNA (bDNA) amplification, Q-Beta replicase, rolling circle replication, rolling circle amplification, or any other nucleic acid amplification method, followed by detection of the amplified molecules using any technique as would be appreciated by one of skill in the art.

In some embodiments, the nucleic acid detection method may be carried out in micro-droplets or other micro-reaction chamber so that the detection method can be run in a highly parallelized manner. In some embodiments, micro-droplets or micro-reaction chambers may contain either 0 or 1 copies of the viral DNA region targeted for detection.

In embodiments involving emulsion PCR, a target nucleic acid or polynucleotide sequence is typically dispersed into micro-droplets. In some embodiments, it is essential that the target nucleic acids be emulsified at a concentration where each micro-droplet (or droplet) contains either one or zero copies of the target molecule. In the case of plasma or serum DNA isolated from patient blood samples, the appropriate dilution level can be recognized by assessing the abundance of a control genomic region and assuring that the frequency of positive micro-droplets remain less than 10% (<10%). The control genomic region detects human (i.e., non-viral) DNA and serves as a quality control for the sample (since many negative samples will not have any positive signal in the assay), and will also be used to establish that the concentration of DNA fragments is appropriate (not to low and not too high).

Within each micro-droplet, the principles of conventional PCR also apply, where the target molecule is amplified by reaction with at least one oligonucleotide primer or pair of oligonucleotide primers. The primer(s) hybridize to a complementary region of the target nucleic acid and a DNA polymerase extends the primer(s) to amplify the target sequence. Under conditions sufficient to provide polymerase-based nucleic acid amplification products, a nucleic acid fragment of one size dominates the reaction products (the target polynucleotide sequence which is the amplification product). The amplification cycle is repeated to increase the concentration of the single target nucleic acid or polynucleotide sequence within each micro-droplet. The reaction can be performed in any thermocycler commonly used for PCR.

Methods for setting up a PCR reaction are well known to those skilled in the art. Any known DNA polymerase, nucleoside triphosphate, buffers, additives/reaction enhancers and conditions for amplification (cycles of denaturation, annealing and polymerization) as would be appreciated by one of skill in the art may be used in the PCR reaction.

In some embodiments, the reaction includes a sequence-specific, hydrolysis probe that is conjugated to both a fluorescent molecule and a fluorescence-quenching molecule to the reaction mixture to enable the detection of successful amplification of the target molecule within each droplet. The chemical composition of specific probes may vary, but follow an established method for detecting synthesis-based nucleic acid amplification by those skilled in the art.

The preparation of an emulsion of the PCR reaction can be achieved in a variety of ways that are appreciated by those versed in the art. One effective methodology utilizes a fabricated microfluidic chip that mixes the aqueous PCR reaction with a lipid solution at controlled pressure to generate micro-droplets of uniform size. The disclosed method is applicable to any method for achieving a partitioned PCR reaction mixture that allows the simultaneous detection of two or more viral nucleic acid target molecules.

Following preparation of a PCR reaction mixture that has been appropriately emulsified or partitioned into droplets, the reaction mixture is subjected to primer extension reaction conditions ("conditions sufficient to provide polymerase-based nucleic acid amplification products"), i.e., conditions that permit for polymerase mediated primer extension by addition of nucleotides to the end of the primer molecule using the template strand as a template. Cycles of denaturation, annealing and polymerization may be performed according to any conditions (e.g., number of cycles, temperatures and duration in time) that would be appreciated by one of skill in the art.

Cycles of denaturation, annealing and polymerization may be performed using an automated device, typically known as a thermal cycler. Thermal cyclers that may be employed are described elsewhere herein as well as in U.S. Pat. Nos. 5,612,473; 5,602,756; 5,538,871; and 5,475,610.

In other embodiments, non-PCR based applications may be used to detect a target nucleic acid sequence, for example, where such target may be immobilized on a solid support. Methods of immobilizing a nucleic acid sequence on a solid support are known in the art and are described in Ausubel et al. Current Protocols in Molecular Biology, John Wiley and Sons, Inc. and in protocols provided by the manufacturers, e.g. for membranes: Pall Corporation, Schleicher & Schuell, for magnetic beads: Dynal, for culture plates: Costar, Nalgenunc, and for other supports.

Other nucleic acid amplification procedures will be appreciated by one of skill in the art, such as, but not limited to, LCR, TAS, 3SR, NASBA, SDA, bDNA, and isothermal amplification. The disclosed method is not limited to the use of amplification by PCR, but rather includes the use of any nucleic acid amplification methods or any other procedures which may be useful in amplification of the sequences for the detection and/or quantification of the presence of or expression of one or more of the particular nucleic acid sequences described herein.

Variations on the exact amounts of the various reagents and on the conditions for the PCR or other suitable amplification procedure (e.g., buffer conditions, cycling times, etc.) that lead to similar amplification or detection/quantification results are known to one of skill in the art and are considered to be equivalents.

Detection of the presence of target molecules in a sample/micro-droplet is not particularly limited, and may be accomplished by any technique appreciated by one of skill in the art. In some embodiments, detection may include hybridization of the target molecule with a target-specific probe, such as a nucleic acid probe, linked to a fluorescent marker. In other embodiments, the marker may be a non-fluorescent marker. The nature of the marker, fluorescent or non-fluorescent, is not particularly limited and may be any marker or label as would be appreciated by of skill in the art.

The detection and distinguishing of partitions (droplets) that contain a target molecule from partitions that contain zero target molecules is a critical step in digital PCR. This can be achieved using a variety of established techniques. In some embodiments, micro-droplets are analyzed individually using a microfluidic channel and a fluorescence detector. Alternatively, advanced microscopy techniques may be implemented to count positive and negative droplets. The disclosed method may be embodied with any nucleic acid detection method.

While some methods disclosed herein have been implementing using digital PCR, the disclosed methods can in principle be utilized with any nucleic acid detection method that is capable of detecting single nucleic acids and distinguishing the size of the detected fragments. For example, such methods may include, hybridization of non-amplified target molecules with a fluorescent or a non-fluorescent probe, and the like. In any such embodiments, the disclosed methods can be applied to distinguish tumor-derived viral nucleic acids in circulation from other non-malignant sources of circulating viral nucleic acid and intact virions. Particular aspects of the disclosed methods are the simultaneous detection in a partitioned reaction of at least two fragments of DNA separated by a defined distance in the viral genome, where the presence of both targets in separate partitions is indicative of tumor viral nucleic acid in a bodily fluid, such as the blood, wherein an increased frequency of co-occupancy of both fragments in the same partition is indicative of non-malignant viral nucleic acids.

The present invention is more particularly described in the following examples that are intended as illustrative only since numerous modifications and variations therein will be apparent and understood to those skilled in the art. Examples of how the application of this specific and sensitive method for detecting tumor viral nucleic acids in a bodily fluid, such as blood, can be used to predict patient prognosis during cancer treatment, and to identify patients who are at the highest risk of disease recurrence among a cohort of patients who are clinically asymptomatic and thought to be in disease remission are provided below.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Digital PCR Assay to Detect HPV viral DNA in Circulating Cell-Free DNA Provided here is an embodiment of the disclosed methods that uses digital emulsion PCR to detect tumor-derived viral HPV DNA in the circulating cell-free DNA isolated from blood. The methodological details described in this example, for example the nucleic acid amplification and detection methods used, are included solely to establish that the invention has been reduced to practice. The methodological details provided in this example related only to this particular embodiment are not to be construed as limiting the invention, as described in the claims and summary sections of this document.

Materials

Reagents: Cell-Free DNA BCT tubes, RUO (Streck catalog No. #218962); QIAamp Circulating Nucleic Acid Kit, Catalog #55114; dPCR Supermax Bio-Rad catalog no #186-3024; Eppendorf™ 96-Well Twin.Tec™ PCR Plates; Fisher Scientific Catalog No. #E951020362; Pipet tips (Bio-Rad catalog No. #186-4121 or #186-4120); Cartridge (Bio-Rad catalog No. #186-4109 or #186-4108); Sealing foil (Bio-Rad catalog No. #181-4040); Optional: VacConnectors (Qiagen Cat No./ID: 19407). This extra connector is useful in case something goes wrong with connectors available in QIAamp Circulating Nucleic Acid Kit, Catalog #55114; Bovine Serum Albumin (BSA); Qubit™ dsDNA HS Assay Kit (Thermo Fisher Scientific Catalog number: #Q32851); Qubit™ Assay Tubes (Thermo Fisher Scientific Catalog number: #Q32856); Falcon® 15 ml Conical Centrifuge Tubes (Corning Catalog No. #352096); Falcon™ 50 ml Conical Centrifuge Tubes (Corning Catalog No. #352098); Disposable sterile 5 ml, 10 ml and 25 ml Serological Pipets (any good brand); Sterile PCR tubes (Any good brand); Sterile filter tips for capacity 2 µl, 10 µl, 200 µl and 1200 µl (any good brand); primers and probes.

Instruments: Microcentrifuge (suitable for 1.5 ml Eppendorf tubes, e.g. Eppendorf 5424 Microcentrifuge); Centrifuge (Suitable for 15 ml falcon tubes, e.g. Eppendorf Centrifuge 5810 R); Qubit Fluorimeter (Thermo Fisher Scientific Catalog No. #Q33226); Deep 96 well thermocycler (Bio-Rad's C1000 Touch™ Thermal Cycler with 96—Deep Well Reaction Module #1851197); Heating block for drying 1.5 ml Eppendorf tubes (Denville Scientific catalog No. #10540); Water bath (should have sufficient space for incubating twenty-four 50 ml Conical Centrifuge Tubes as 24 samples can be processed at one time); Automated droplet generator (Bio-Rad catalog No. #186-4101); Bio-Rad QX200™ Droplet Reader Catalog No. #1864003; Portable Pipet-Aid® XP Pipette Controller (Drummond Scientific, Catalog No. 4-000-101); Pipette (capacity: 2 µl, 10 µl, 20 µl, 200 µl and 1000 µl; any good brand); 8-channel pipette (any good brand, e.g. Eppendorf Catalog No. #3125000010).

Methods

Blood Collection: Blood is collected in Cell-Free DNA BCT tubes, RUO (Streck catalog No. #218962).

Plasma Extraction: Collected blood from step I should ideally be processed on the same day to extract plasma. Same tube can be centrifuged at 2000×g for 10 min at room temperature (RT). Supernatant is transferred to new Falcon™ 15 mL Conical Centrifuge Tubes. Care should be taken to avoid taking middle whitish layer below plasma. Centrifuge the tube again for 10 min at 2000×g at RT. Supernatant is then transferred to a new Falcon™ 15 ml Conical Centrifuge Tubes. The plasma is at −80° C. freezer till further use. NOTE: sometimes 10 min. centrifuge does not lead to clear separation of plasma layer. In such situation, sample should be centrifuged for another 10 min before taking out the plasma. Or, alternatively centrifugation at first step can be done for 15-20 min. Record the sample if plasma looks red. Sometimes extra processing of the sample is required during PCR step because of the hemolysis. Blood should be discarded in 10% bleach or autoclaved or according to any other institution/company approved protocol.

Plasma cell free DNA (cfDNA) Extraction: The stored plasma samples are thawed at 37° C. in a water bath for about 5 min. A Qiagen kit (QIAamp Circulating Nucleic Acid Kit, Catalog #55114) is used to extract DNA using manufacturer's protocol with the following modifications: Standard vacuum available in laboratory can be used in the protocol; The cfDNA is eluted in 2 steps—first with 100 µl elution buffer and then 75 µl elution buffer if plasma volume is more than 3 ml. Elution can be done in lower volume if the collected plasma volume is less to avoid excessive dilution of the cfDNA; and it was observed that incubation of the column for 3 min. after adding elution buffer (as suggested in the protocol) does not lead to the complete extraction of cfDNA. Generally, a 30 min to 1 h incubation at RT generally follows both elution steps. The cfDNA is quantified on a Qubit fluorimeter. (Note: Generally, 2 µl of the eluate is sufficient to be used for quantification purpose).

The eluted cfDNA is stored at −20° C. freezer until further use. Note: The cfDNA recovered at first elution is used for all experiments and calculations. The cfDNA recovered in the second elution step is used only if cfDNA at first elution is exhausted. If a more concentrated cfDNA is required for any purpose like NGS, then the sample can be concentrated using speed vacuum.

dPCR: The dPCR involve three steps—Droplet generation; PCR; and droplet reading.

Droplet Generation: Prepare 25 μl reaction for each sample customized as per the following composition (Reagents: dPCR Supermax Bio-Rad catalog no #186-3024; any nuclease free PCR grade water can be used; other reagents like forward primer, reverse primer and probe are designed by user)

TABLE 1

Reaction Mixtures

| Component | Working stock | Final Conc. | 1x (sample) | 1x No template control (NTC) |
|---|---|---|---|---|
| Primers Mixture (4) | 22.5 μM each | 0.9 μM each | 1 μl | 1 μl |
| Probes Mixture (2) | 6.25 μM each | 0.125 μM each | 0.5 μl | 0.5 μl |
| Albumin | 10% | 0.4% | 1 μl | 1 μl |
| Betaine | 5M | 0.4 μM | 2 μl | 2 μl |
| Trehalose | 1.25M | 0.16M | 3.2 μl | 3.2 μl |
| dPCR Supermix | 2x | 1x | 12.5 μl | 12.5 μl |
| DNA sample | 1x/Diluted | N/A | 4.3 μl | — |
| PCR grade Water | Adjustable | N/A | — | 4.3 μl |
| Total | | | 25 μl | 25 μl |

The primer and probe sequences for the ctHPVDNA assay described here are as follows:

TABLE 2

Primers and Probes

| Variant | Primers/Probes |
|---|---|
| HPV16 Fragment 1 | 283_HPV-16_F1 For: TGACTCTACGCTTCGGTTG (SEQ ID NO: 1) 284_HPV-16_F1 Rev: GCCCATTAACAGGTCTTCC (SEQ ID NO: 2) 420_HPV-16_F1 Probe_FAM-ZEN_v2: CGTACAAACACACAGTAGACATTCGTAC (SEQ ID NO: 3) |
| HPV16 Fragment 2 | 424_HPV16_F2 For: GGTTTGTAACATCCCAGGC (SEQ ID NO: 4) 425_HPV16_F2_Rev: GTGTATTTTTTAAGGGGATCTTCTT (SEQ ID NO: 5) 421_HPV16_F2_HEX_LNA: CACCT(+C)(+C)A(+G)CACC (SEQ ID NO: 6) |

"(+N)" denotes LNA™ base

The Primers mixture working stock is assembled by combining 22.5 μL each of the four primers (100 μM concentration) into a tube and adding 10 μL nuclease-free water to achieve a final concentration of 22.5 μM for each primer.

The Probe mixture working stock is assembled by combining 6.25 μL of each probe (100 μM concentration) into a tube and adding 87.5 μL nuclease-free water to achieve a final concentration of 6.25 μL for each probe.

About 22-23 μl of the above reaction mixture is loaded on a 96 well plate (Eppendorf™ 96-Well Twin.Tec™ PCR Plates, Fisher Scientific Catalog No. #E951020362) using Multichannel Pipettors (Note: Instrument uses only 20 μl from each well. An extra volume is added to avoid any pipetting error) Droplets are generated using automated droplet generator (Bio-Rad catalog No. #186-4101) following manufacturer's protocol. Reagents required at this step are pipet tips (Bio-Rad catalog No. #186-4121 or # 186-4120) and cartridges (Bio-Rad catalog No #186-4109 or #186-4108). The sample plate is sealed with sealing foil (Bio-Rad catalog No. #181-4040) following manufacturer's protocol. Note: The volume of cfDNA+water should be 4.3 μl. Generally, there is no issue by using 4.3 μl of cfDNA sample in the reaction but sometimes the allele copy number is too high and it results in streaking of the positive droplet across the axis and many dual positive droplets. In such cases, the run should be repeated by using less sample and remaining volume can be adjusted with water. Dilution gives better quantification of allele frequency in such cases. A linear relationship across 5 orders of magnitude has been observed in HPV16 copy number ranging from 5 copies to 50,000 copies per 20 μl reaction. Care should be taken to seal the plate properly. If the plate is not sealed properly then it will lead to sample evaporation during PCR step.

PCR: The PCR thermocycling was performed using the protocol as described below.

TABLE 3

PCR conditions

| Cycling step | Temperature, ° C. | Time | Ramp Rate | Number of Cycles |
|---|---|---|---|---|
| Enzyme activation | 95 | 10 sec | 2° C./sec | 1 |
| Dentaturation | 94 | 30 sec | | 40 |
| Annealing | 60 | 1 min | | 40 |
| Extension | 68 | 1 min | | 40 |
| Enzyme deactivation | 98 | 10 min | | 1 |
| Hold (optional) | 4 | Infinite | | 1 |

Use a heated lid set to 105° C. and set the sample volume to 40 μl

All wells should be observed visually after PCR and before reading the plate on droplet reader. The copy numbers observed during droplet reading may not be real if there is any well where sample is evaporated because of improper sealing. It is good to leave the plate in the thermocycler for about 15-20 min after PCR is done. It allows the temperature of the plate to come down at more controlled way and it avoids droplet malformation. Sometimes malformation of the droplets because of the static current can be avoided by touching hand with other metallic surface before taking out the plate from thermocycler. It should be made a routine practice for better reproducibility of the results. The PCR plate can be stored overnight after PCR and reading can be done next day morning if time is limited. However, finishing everything in one day is best practice.

Droplet Reading: The droplet reader (Bio-Rad QX200™ Droplet Reader Catalog No. #1864003) is used to read signal in droplets following the manufacturer's protocol. Note: Discarding Oil waste: The composition of droplet reader oil is proprietary of Bio-Rad. A typical waste profile contains fluorinated oils (95%), water (5%), bleach (<0.5%), proteins, nucleic acids, and fluorescent dye (<0.1%). A proper disposal should be planned accordingly.

Data Analysis: The copy number calculations should be done following the manufacturer's guidelines. An example of the dPCR ctHPVDNA assay readout is shown in FIG. 1A. The following parameters were set for calculation of FAM-single positive, HEX-single positive, and FAM+HEX double positive droplets. In the FAM channel, a cutoff of 700 is used to separate the negative from positive droplets. Similarly in the HEX channel, a cutoff of 3000 is used to separate the negative from positive droplets. The FAM+HEX double positive droplets are those with >700 fluorescence intensity in the FAM channel and >3000 fluorescence intensity in the HEX channel. The double negative droplets have FAM fluorescence <700 and HEX fluorescence <3000.

Poisson statistics is used to calculate the copies of each fragment in the reaction individually, using the following formula:
copies=#total droplets*ln (#total droplets/#signal negative droplets). This is calculated first for fragment 1 (FAM positive) and for fragment 2 (HEX positive).

Extensive control assays have been run to determine the level of experimental noise. Based on these controls, the following criteria were used to determine the number of copies of the target fragment (s) in the assay reaction.

TABLE 4

Control Criteria

| HPV16 copies/ 20 µl reaction | Considered as |
|---|---|
| 0 | Zero |
| Below 3 | False positive and should be considered as zero |
| 3-5 | Assay should be repeated to confirm the value |
| Above 5 | Considered as positive for HPV16 |
| Any positive value in follow up patient when previous HPV16 values are negative | Assay should be repeated to confirm the value |

Figure 1B:
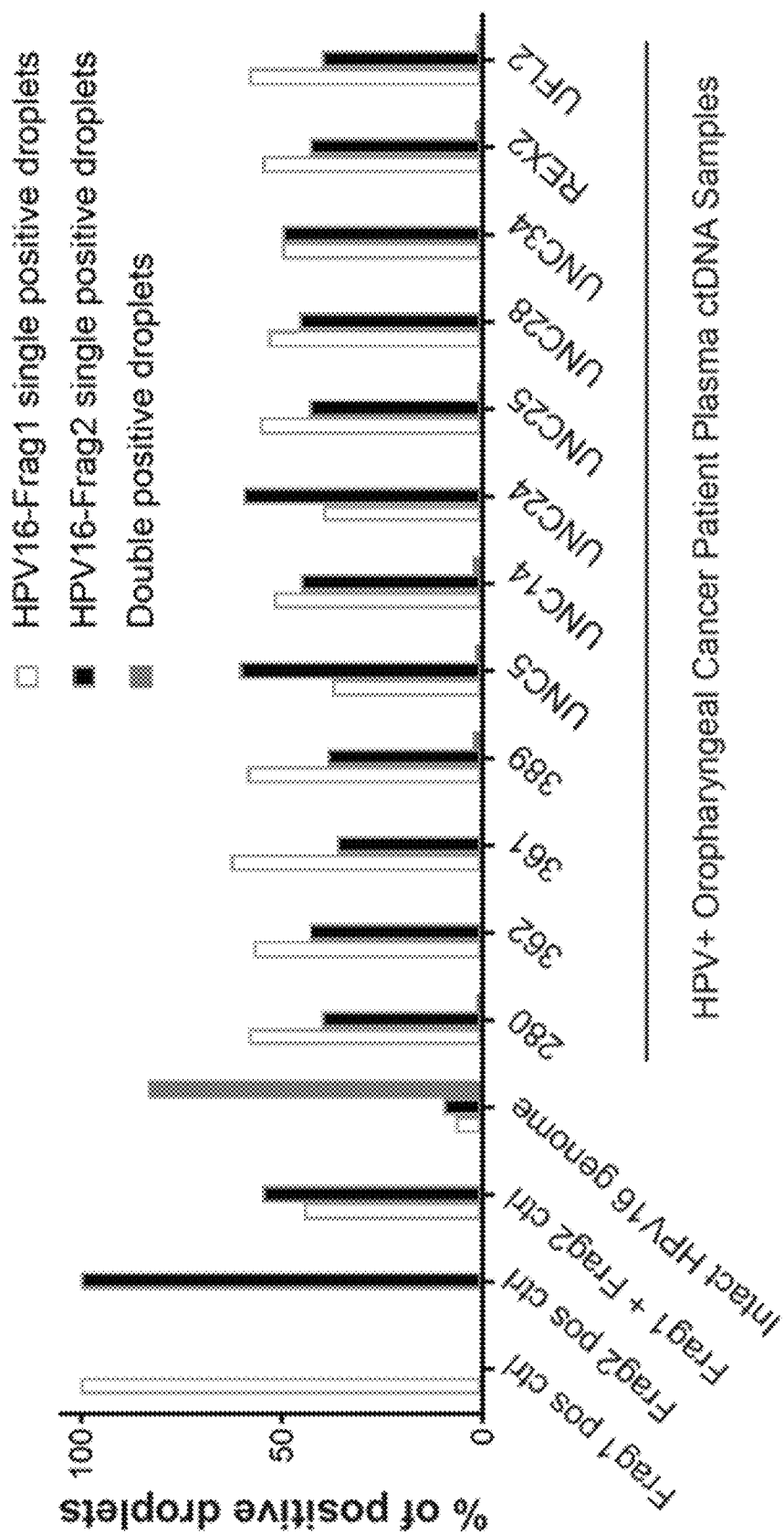

These copy number values can be used to calculate the frequency of a droplet possessing the target fragment: Pr (frag)=(#positive droplets/#total droplets). The frequency of double-positive droplets that are expected if the sample consists of fragmented, circulating tumor viral DNA is estimated as: Pr (double positive)=Pr (frag1)*Pr(frag2). In contrast, if the Pr (dual positive)>2*Pr (frag1)*Pf (frag2), then the sample was considered to contain non-fragmented viral DNA that is not tumor-derived. If Pr (double positive) >Pr (frag1) or Pr (double positive)>Pr (frag2) it was interpret that the sample is negative for circulating tumor-derived viral nucleic acids. If Pr (frag1) AND Pr (frag2)>2*Pr (double positive), then the sample was considered positive for circulating tumor-derived viral nucleic acids, although there is evidence for coexistent non-tumor derived viral nucleic acids. Raw data for this assay applied to experimental controls and plasma DNA from a cohort of 12 patients with HPV+ oropharyngeal cancer is shown in FIG. 1A-1B.

For the HPV16 F1 assay, cutoff of 700 was set on y-axis (FAM channel). Any droplets above 700 are considered as positive droplets for HPV16. For the HPV16 F2 assay, a cutoff of 3000 was set on x-axis (Hex channel). Any droplets above 3000 was considered as positive droplet for HPV16 F2. Occasionally, the patterns of the dPCR readout look unusual. This can be because of a bad sample (unanalyzable cfDNA) or a bad dPCR run. Such sample should be repeated to fix the problem. Data from such samples cannot be used for interpretation. If sample quality is not improved with any available strategies then sample should be categorized as unanalyzable DNA or bad sample. Some strategies to improve the sample quality are as below. The presence of Heparin in the blood sample can interfere with the dPCR reaction. Treating the sample with Bacteroides Heparinase I (New England Biolabs cat no. #P0735S) using manufacturer's protocol improves the quality of sample. Excessive hemolysis sometimes interferes with the dPCR. An improvement has been observed in the assay readout by adding 0.4% bovine serum albumin Some of the representative dot plots from bad samples are provided as separate file with suggested solutions.

Using an endogenous genomic sequence as a positive control for the dPCR reaction is essential for validating sample quality. dPCR-based detection of a target sequence in the ESR1 gene was utilized as a positive control for sample quality. The assay is described below:

TABLE 5

| Variant | Primers and Probes |
|---|---|
| Genomic Control (ESR1 locus) | 132_CtrlESR1_F2: ATCTGTACAGCATGAAGTGCAAGA (SEQ ID NO: 7) 133_CtrlESR1_R2: CTAGTGGGCGCATGTAGGC (SEQ ID NO: 8) 094_CtrlESR1_LNA2-TET_probe_WT: T(+C)(+T(+A)T(+G)(+A)(+C)CTG (SEQ ID NO: 9) |

"(+N)" denotes LNA™ base

TABLE 6

Setting PCR Reaction

| Component | Working stock | Final conc. | 1x (sample) | 1x (NTC) |
|---|---|---|---|---|
| Forward primer | 22.5 µM | 0.9 µM | 1 µl | 1 µl |
| Reverse primer | 22.5 µM | 0.9 µM | 1 µl | 1 µl |
| Probe | 6.25 µM | 0.25 µM | 1 µl | 1 µl |
| BSA | 10% | 0.4% | 1 µl | 1 µl |
| dPCR Supermix | 2x | 1x | 12.5 µl | 12.5 µl |
| DNA sample | Neat/diluted | N/A | 8.5 µl | — |
| PCR grade Water | Adjustable | N/A | — | 8.5 µl |
| Total | | | 25 µl | 25 µl |

TABLE 7

PCR Conditions

| Cycling step | Temp, ° C. | Time | Ramp Rate | Number of Cycles |
|---|---|---|---|---|
| Enzyme activation | 95 | 10 sec | 2° C./ sec | 1 |
| Denaturation | 94 | 30 sec | | 40 |
| Annealing/Extension | 60 | 1 min | | 40 |
| Enzyme deactivation | 98 | 10 min | | 1 |
| Hold (optional) | 4 | Infinite | | 1 |
| Use a heated lid set to 105° C. and set the sample volume to 40 µl | | | | |

Work Flow for the analysis of plasma DNA samples:
1) Test samples using ESR1 genomic control dPCR assay, to evaluate amplifiable DNA and sample concentration.

2) Test the samples for the dual fragment HPV16 assay (HPV16ZENv2)

4) If sample is negative for HPV16 then perform the HPV multiplexed assay (HPVmultiplexed_v1)

5) Perform the duplex assay to know specific HPV variant

Example 2: Multiplexed dPCR Assay to Detect 5 Distinct HPV Sub-Strains (HPVmultiplexed_v1)

The disclosed methods were applied to sub-strains of a given virus. While the embodiment here relates to sub-strains of the HPV virus, the method can be readily applied to other viral sub-strains using established techniques known to those versed in the field. Variants included in the described embodiment of the method are HPV16, HPV18, HPV31, HPV33 and HPV35

HPV16 probe was tagged with FAM-Zen while others with HEX (LNA version).

TABLE 8

Primers and Probes

| Variant | Primers and Probes |
|---|---|
| HPV16 | 283_HPV-16_For:<br>TGACTCTACGCTTCGGTTG<br>(SEQ ID NO: 1)<br>284_HPV-16_Rev:<br>GCCCATTAACAGGTCTTCC<br>(SEQ ID NO: 2)<br>420_HPV-16_Probe_FAM-ZEN_v2:<br>AGTACAAAGCACACACGTAGACATTCGTAC<br>(SEQ ID NO: 3) |
| HPV18 | 401_HPV18_For:<br>TGAAGCCAGAATTGAGCTAG<br>(SEQ ID NO: 10)<br>422_HPV18_Rev_v2:<br>AGGACAGGGTGTTCAGAA<br>(SEQ ID NO: 11)<br>403_HPV18_LNA_HEX-Probe:<br>CA(+G)A(+C)(+G)AC(+C)TTCG<br>(SEQ ID NO: 12) |
| HPV31 | 404_HPV31_For:<br>AGCACACAAGTAGATATTCGC<br>(SEQ ID NO: 13)<br>405_HPV31_Rev:<br>TAGTAGAACAGTTGGGGCA<br>(SEQ ID NO: 14)<br>406_HPV31_LNA_HEX-Probe:<br>TAA(+C)(+A)(+G)(+C)T(+C)(+T)TG(+C)<br>(SEQ ID NO: 15) |
| HPV33 | 407_HPV33_For:<br>TAACACCACAGTTCGTTTATGT<br>(SEQ ID NO: 16)<br>423_HPV33_Rev_v2:<br>ACAATATTCACTGTGCCCATA<br>(SEQ ID NO: 17)<br>418_HPV33_LNA_HEX-Probe_v2:<br>TG(+A)C(+C)(+T)A(+C)G(+A)(+A)CC<br>(SEQ ID NO: 18) |
| HPV35 | 410_HPV35_For:<br>TGAGGCGACACTACGTC<br>(SEQ ID NO: 19)<br>411_HPV35_Rev:<br>GTGCCCATTAATAAATCTTCCAA<br>(SEQ ID NO: 20)<br>419_HPV35_LNA_HEX-Probe_v2:<br>AG(+A)G(+C)(+A)CA(+C)(+A)CAT<br>(SEQ ID NO: 21) |

"(+N)" denotes LNA™ base

Reaction Mixture

Primer mixture: Mix equal volume of 10 primers each at 100 μM (each primer diluted 1:10 in the mixture). Probe mixture: Mix 6.25 μl of each of five probes in a tube and add 68.75 μl water (final concentration will be 6.25 μM each in 100 μl volume)

TABLE 9

Reaction Mixtures

| Component | Working stock | Final Conc. | 1x (sample) | 1x (NTC) |
|---|---|---|---|---|
| Primers Mixture | 10 μM each | 0.9 μM each | 2.25 μl | 2.25 μl |
| Probes Mixture | 6.25 μM each | 0.125 μM each | 0.5 μl | 0.5 μl |
| Albumin | 10% | 0.4% | 1 μl | 1 μl |
| Betaine | 5M | 0.4 μM | 2 μl | 2 μl |
| Trehalose | 1.25M | 0.16M | 3.2 μl | 3.2 μl |
| dPCR Supermix | 2x | 1x | 12.5 μl | 12.5 μl |
| DNA sample | Neat/Diluted | N/A | 3.55 μl | — |
| PCR grade Water | Adjustable | N/A | — | 3.55 μl |
| Total | | | 25 μl | 25 μl |

TABLE 10

PCR conditions

| Cycling step | Temperature, ° C. | Time | Ramp Rate | Number of Cycles |
|---|---|---|---|---|
| Enzyme activation | 95 | 10 sec | 2° C./sec | 1 |
| Dentaturation | 94 | 30 sec | | 40 |
| Annealing | 60 | 1 min | | 40 |
| Extension | 68 | 1 min | | 40 |
| Enzyme deactivation | 98 | 10 min | | 1 |
| Hold (optional) | 4 | Infinite | | 1 |

Use a heated lid set to 105° C. and set the sample volume to 40 μl

Note:
An LNA ™-FAM probe was also designed to amplify common region in all known HPV16 variants with same primers (No. 283 & 285). This was not used in the multiplexed assay.

413 HPV16 LNA_FAM-CommonProbe: CA(+C)A(+C)(+G)(+T)A(+G)(+A)CAT (SEQ ID NO:22)

Example 3: Duplex dPCR Assay to Detect Specific HPV Variants (HPV_18&33_v1 and HPV_31&35_v1)

This assay was designed to know the identity of specific HPV variants in patient samples.

TABLE 11

Primers and Probes

| | Variant | Primers | Probe |
|---|---|---|---|
| Set 1 | HPV18 & HPV33 | 401_HPV18_For:<br>TGAAGCCAGAATTGAGCTAG<br>(SEQ ID NO: 10)<br>422_HPV18_Rev_v2:<br>AGACAGGGTGTTCAGAA<br>(SEQ ID NO: 11) | |

TABLE 11-continued

Primers and Probes

| Variant | Primers | Probe |
|---|---|---|
| | 407_HPV33_For: TAACACCACAGTTCGTTTATGT (SEQ ID NO: 16) 423_HPV33_Rev_v2: ACATATATTCACTGTGCCCATA (SEQ ID NO: 17) | 403_HPV18_LNA_HEX-Probe: CA(+G)A(+C)(+G)AC+CTTCG (SEQ ID NO: 12) 426_HPV33_LNA_FAM-Probe: TG(+A)C(+C)(+T)A(+C)G(+A)(+A)CC (SEQ ID NO: 18) |
| Set 2 HPV31 & HPV35 | 404_HPV31_For: AGCACACAAGTAGATATTCGC (SEQ ID NO: 13) 405_HPV31_Rev: TAGTAGAACAGTTGGGGCA (SEQ ID NO: 14) 410_HPV35_For: TGAGGCGACACTACGTC (SEQ ID NO: 19) 411_HPV35_Rev: GTGCCCATTAATAAATCTTCCAA (SEQ ID NO: 20) | 406_HPV31_LNA_HEX-Probe: TAA(+C)(+A)G(+C)T(+C)(+T)TG(+C) (SEQ ID NO: 15) 427_HPV35_LNA_FAM-Probe: AG(+A)G(+C)(+A(CA(+C)(+A)CAT (SEQ ID NO: 21) |

"(+N)" denotes LNA™ base

Reaction Mixture

Primer mixture: Mix 22.5 µl of each of the four primers and add 10 µl water (22.5 µM each primer in the mixture). Probe mixture: Mix 6.25 µl of both probes in a tube and add 87.5 µl water (final concentration will be 6.25 µM each in 100 µl volume).

TABLE 12

Reaction Conditions

| Component | Working stock | Final Conc. | 1x (sample) | 1x (NTC) |
|---|---|---|---|---|
| Primers Mixture | 22.5 µM each | 0.9 µM each | 1 µl | 1 µl |
| Probes Mixture | 6.25 µM each | 0.125 µM each | 0.5 µl | 0.5 µl |
| Albumin | 10% | 0.4% | 1 µl | 1 µl |
| Betaine | 5M | 0.4 µM | 2 µl | 2 µl |
| Trehalose | 1.25M | 0.16M | 3.2 µl | 3.2 µl |
| dPCR Supermix | 2x | 1x | 12.5 µl | 12.5 µl |
| DNA sample | Neat/Diluted | N/A | 4.3 µl | — |
| PCR grade Water | Adjustable | N/A | — | 4.3 µl |
| Total | | | 25 µl | 25 µl |

TABLE 13

PCR conditions

| Cycling step | Temperature, °C. | Time | Ramp Rate | Number of Cycles |
|---|---|---|---|---|
| Enzyme activation | 95 | 10 sec | 2° C./sec | 1 |
| Dentaturation | 94 | 30 sec | | 40 |

TABLE 13-continued

PCR conditions

| Cycling step | Temperature, °C. | Time | Ramp Rate | Number of Cycles |
|---|---|---|---|---|
| Annealing | 60 | 1 min | | 40 |
| Extension | 68 | 1 min | | 40 |
| Enzyme deactivation | 98 | 10 min | | 1 |
| Hold (optional) | 4 | Infinite | | 1 |

Use a heated lid set to 105° C. and set the sample volume to 40 µl

Example 4: Application to Patient Blood Samples in Prospective Clinical Trials

Figure 2:
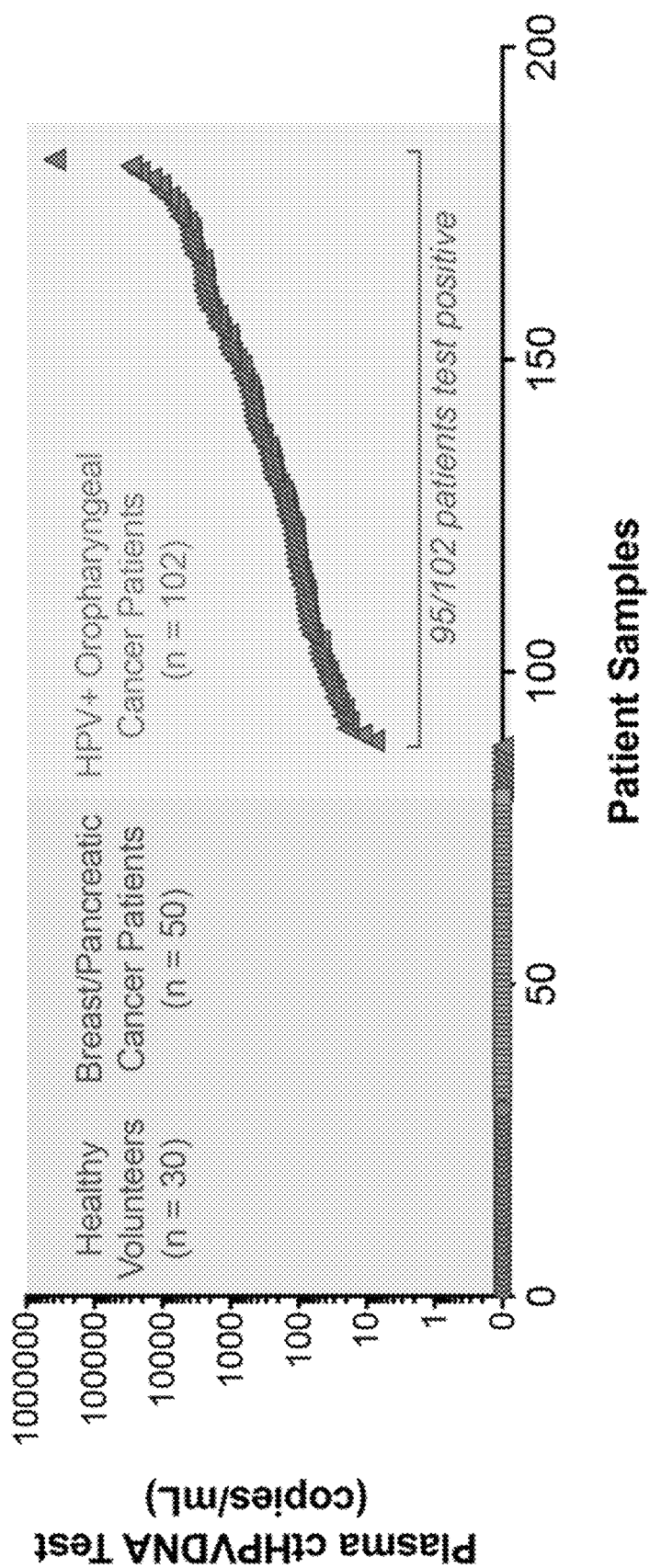
FIG. 2: Analysis of a large cohort of patient blood samples using the HPV blood assay described in Example 1. There was no HPV tumor viral DNA detected in 30 healthy volunteers and 50 patients with HPV negative cancers (breast and pancreatic). In contrast, 95/102 patients with a diagnosis of HPV positive oropharyngeal cancer have pre-treatment circulating tumor HPV DNA in plasma using the blood test described here. The observed number of copies of HPVDNA detected by the assay is also indicated, highlighting the dynamic range of the test. Based on this data, estimates for assay specificity and sensitivity are 100% and 93%, respectively, at the time of initial diagnosis.

Blood samples were analyzed from healthy volunteers, non-virus associated cancer, and HPV+ cancer. Circulating tumor HPV DNA copy numbers, as measured using the assay technology described in Example 1, are shown in FIG. 2. These data indicate that the ctHPVDNA blood test has 100% specificity and 93% sensitivity for identifying patients with HPV+ cancer.

Blood samples were analyzed from patients enrolled in two prospective phase II clinical trials. The disclosed method for specifically detecting tumor-derived viral HPV DNA in the blood was integrated into the design of both of these clinical trials. The findings from these longitudinal clinical studies illustrate the applicability and utility of the disclosed method both for personalizing patient therapy and for cancer surveillance.

Summary of patient cohort and clinical trial design. Two prospective phase II clinical trials were completed that evaluated the efficacy of a de-intensified chemo-radiation therapy regimen in low risk OPSCC. In LCCC 1120 (NCT01530997) 45 patients were treated with de-intensified CRT. Eligible patients had HPV-positive and/or p16-positive OPSCC, T0-T3, N0-N2c, M0, and <10 pack years of smoking. Patients received 60 Gy of Intensity Modulated Radiotherapy (IMRT) with concurrent weekly intravenous cisplatin (30 mg/m$^2$). All patients had biopsy of the primary site and underwent a selective neck dissection to encompass nodal level(s) that were positive pre-treatment, within 4 to 14 weeks after CRT. The primary endpoint of LCCC 1120 was the rate of pCR, which was 86% (37/43) and the 3-year cancer control and overall survival was 100% and 95%, respectively. In addition to excellent cancer control, patient had less toxicity and reported excellent quality of life and lower symptom burden as compared to standard of care CRT (70 Gy). In a second-generation phase 2 study (LCCC 1413, NCT02281955) a 12-week post-treatment PET/CT was used to guide the use of biopsy/neck dissection (i.e. post CRT surgical evaluation was not mandatory, but guided by imaging). Of the 113 patients enrolled, 82 patients have had a minimum of 1-year follow-up and the 2-year actuarial cancer control and overall survival in these 82 patients is 90% and 95% respectively (again excellent results). Patients continue to report good recovery of quality of life at 1 year, and thus supports the concept that dose de-escalation can improve the therapeutic ratio. A third generation phase 2 study (LCCC 1612, NCT03077243) is currently being conducted, and has enrolled 53 of an expected 120 patients. Blood samples from 113 patients were prospectively analyzed to detect tumor-derived plasma viral HPV DNA.

Levels of tumor-derived viral HPV DNA in the blood, as quantified by the disclosed method, correlate significantly with HPV viral DNA in primary tumors. In 63 patients with HPV-OPSCC, serial levels of tumor-derived viral HPV DNA (pre- and weekly during-RT) were prospectively quantified in patient blood samples using the disclosed method (FIG. 3A). 49 patients had detectable tumor-derived viral HPV DNA in the circulation prior to treatment. In all 49 patients, the levels of circulating HPV DNA had dropped significantly by week 6 (FIG. 3B) following the initiating of chemo-radiation therapy, diminishing to undetectable levels in a majority (90%, n=44/49) of patients by the end of the therapeutic regimen. Across patients, the peak levels of tumor-derived viral HPV DNA in the blood, ranged from 10 copies/mL to ~30,000 copies/mL. Moreover, distinct clearance kinetics of tumor-derived viral HPV DNA was observed in the blood during CRT treatment. In one group there was rapid clearance kinetics (FIG. 3C), with >95% of the peak tumor-derived viral HPV DNA in the blood being cleared by day 28 of therapy. In a second group there was delayed clearance of tumor viral HPV DNA in the blood (FIG. 3D), which may be associated with poor or delayed response to therapy.

The disclosed method was further validated by correlating levels of tumor-derived viral HPV DNA in the blood with analysis of matched primary tumors in a cohort of 20 patients (FIG. 4). Normalized HPV DNA copies in tumor biopsy material correlates strongly with HPV DNA copies as measured by next-generation sequencing (FIG. 4A). Moreover, the quantity of tumor-derived viral HPV DNA in blood correlates significantly with HPV DNA copy number in the matched tumor biopsy, after normalizing to the overall tumor burden in the patient (FIG. 4B). Using next-generation sequencing, cancers with integration of HPV into the cancer cell genome were identified (FIG. 4C-4D). Higher copy number of HPV DNA in tumor biopsy material correlated with a high likelihood of episomal (non-integrated) HPV DNA in the matched primary tumor (FIG. 4E). Similarly, higher copy numbers of tumor-derived viral HPV DNA in the blood correlated with a higher likelihood of episomal (non-integrated) HPV DNA in the matched primary tumor (FIG. 4F). These findings validate the disclosed methods by establishing that the quantification of viral DNA in the blood using the disclosed methods correlates significantly with measurements of viral DNA in matched tumor tissue. These observations also demonstrate the disclosed method can monitor the presence and clearance of tumor-derived HPV viral DNA in longitudinal analysis of patient blood samples.

Figure 5A:
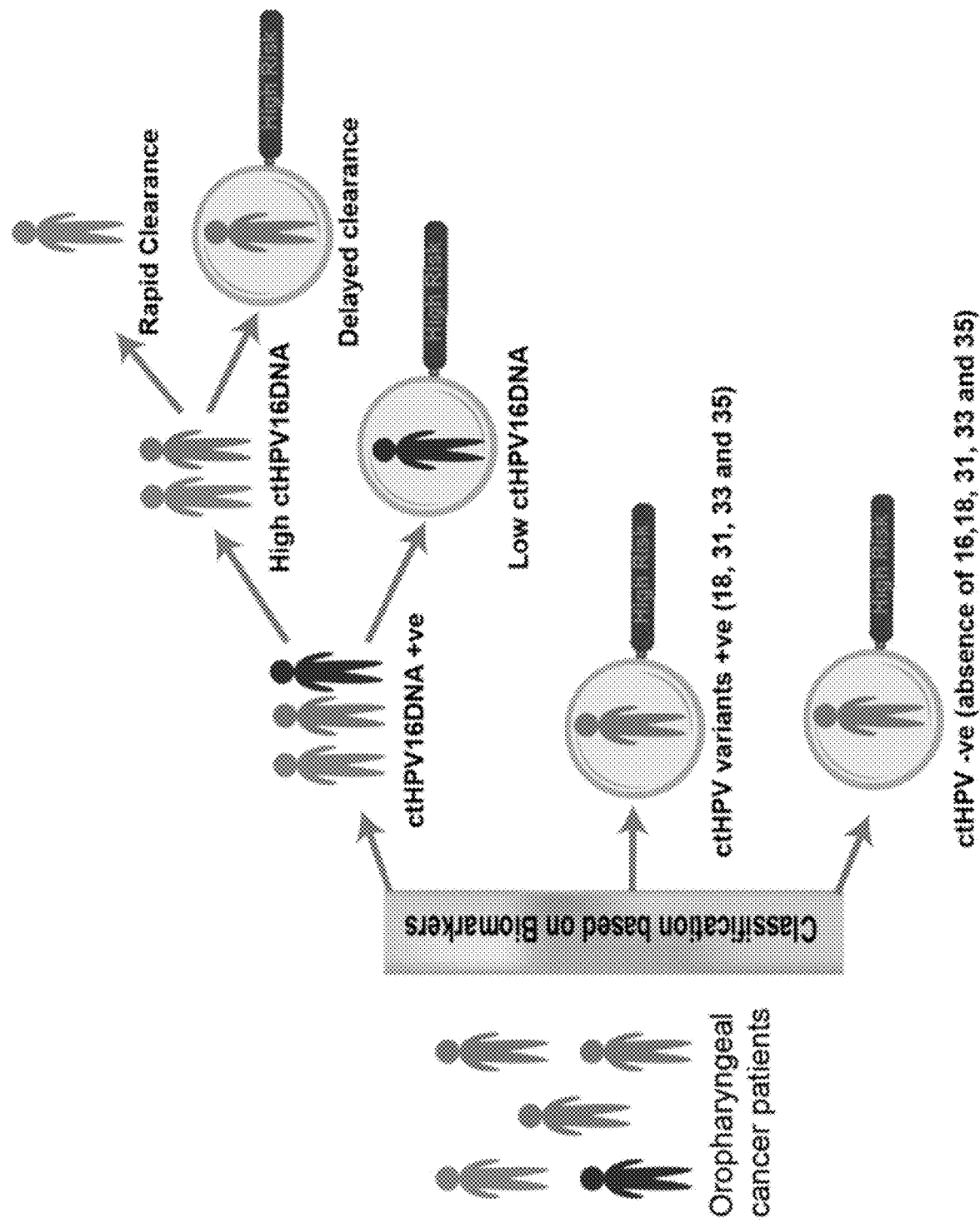
FIG. 5A-B.
Figure 5B:
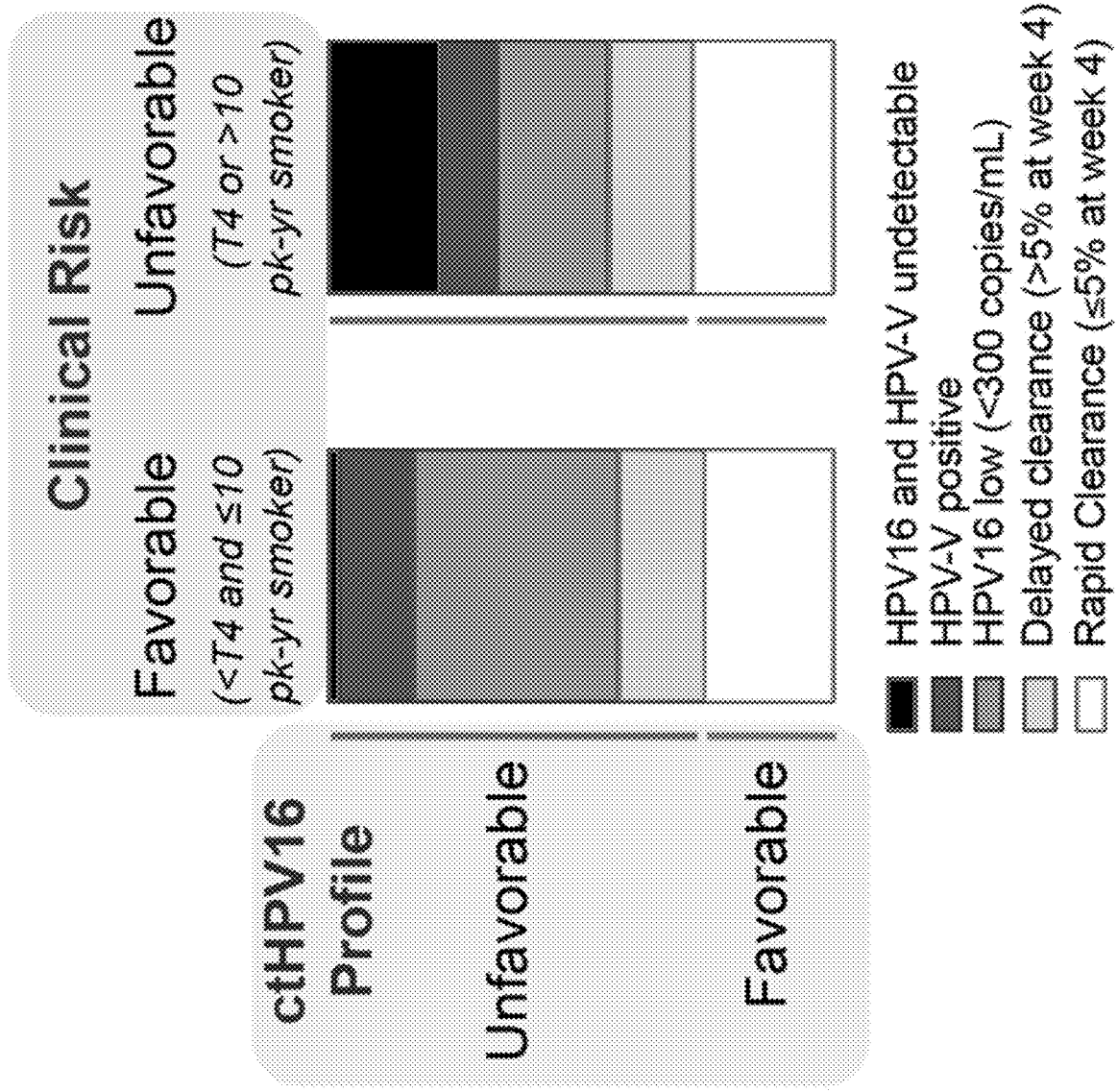
Figure 6A:
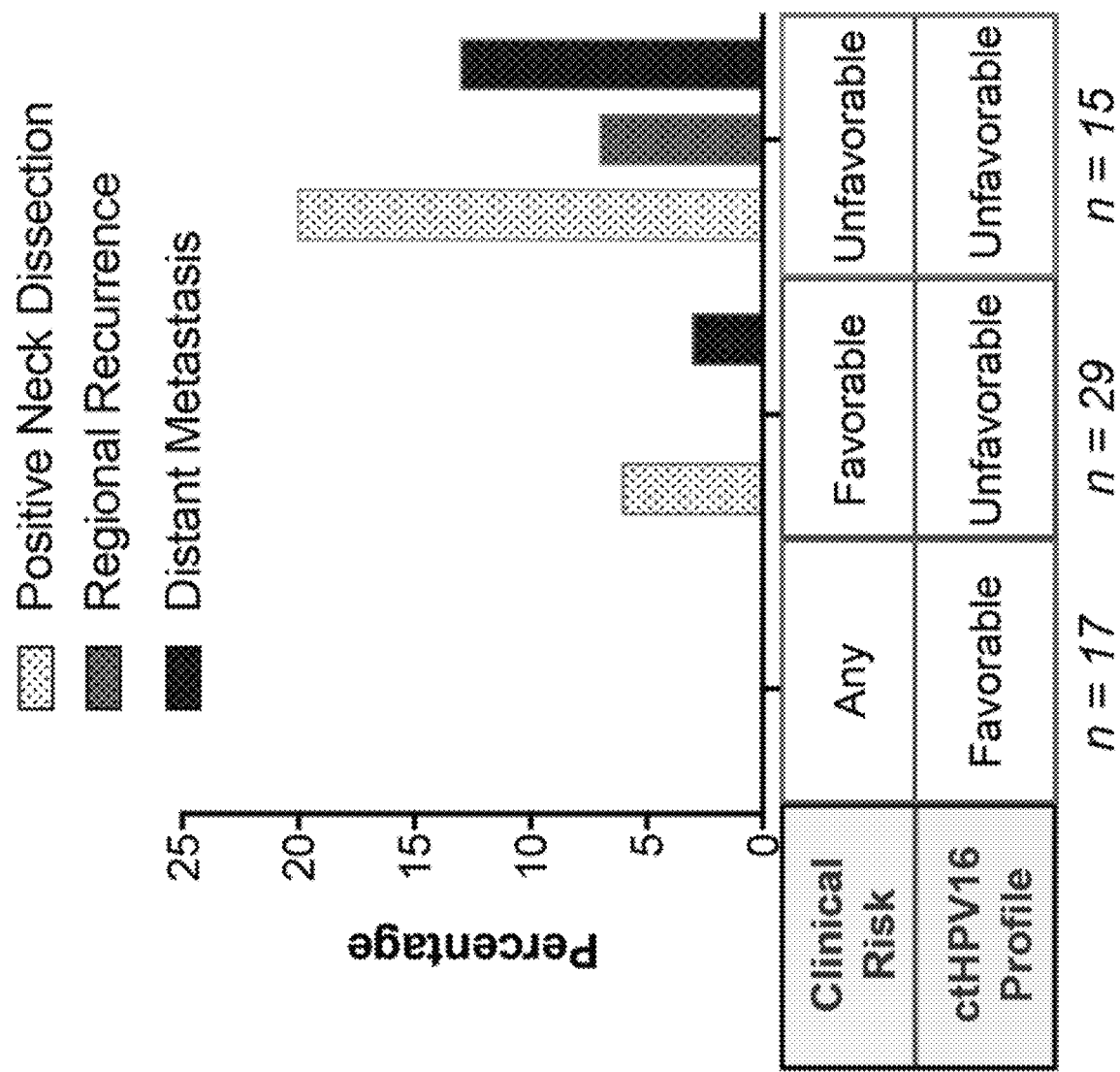
FIG. 6A-B.
Figure 6B:
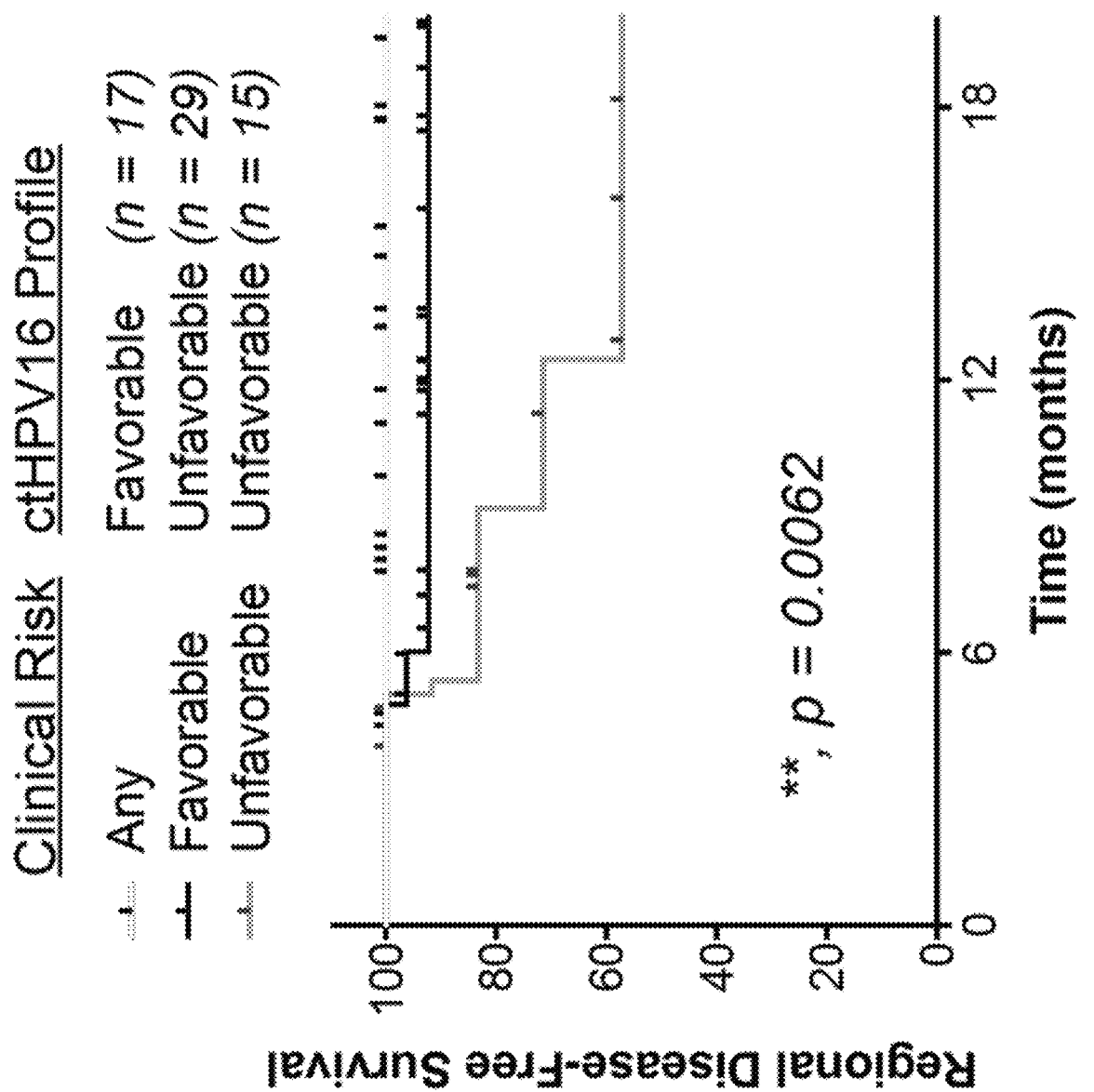

Predict clinical risk in cancer patients. The disclosed method was applied to monitor tumor-derived viral HPV DNA in the blood before and during therapy in 63 patients enrolled in the clinical trial described above. A Favorable Profile was defined as having abundant ctHPV16DNA peak levels of tumor-derived viral HPV DNA in the blood (>200 copies/mL) and rapid clearance kinetics (≤2% of the peak value by week 4) (FIG. 5A). 18 out of 63 evaluable patients (29%) had a Favorable Profile (FIG. 5B), and none of these 18 patients have recurred (regardless of smoking status) (FIG. 6A-B). An Unfavorable Profile was defined as (i) undetectable pre-treatment tumor-derived viral HPV DNA in the blood, (ii) low peak values of tumor-derived viral HPV DNA in the blood (≤200 copies/mL), or (iii) >2% of the peak value by week 4 (40 Gy) (FIG. 5A-B). Remarkably, patients with a Favorable Profile exhibited 100% disease control in non-smokers (60 Gy) and heavy smokers (60-70 Gy). In contrast, heavy smokers (>10 pack year) with an Unfavorable Profile had a very poor regional disease control rate of 45% at 12 months after completing therapy (FIG. 6A-B). These observations demonstrate the clinical utility of applying the disclosed method to quantify tumor-derived viral DNA in the blood as a biomarker to predict clinical risk among virus-associated cancer patients. Moreover, these findings indicate that a real-time assessment of circulating tumor-derived viral DNA can be utilized to personalize the intensity of therapy for patients based on their inferred risk.

Figure 7:
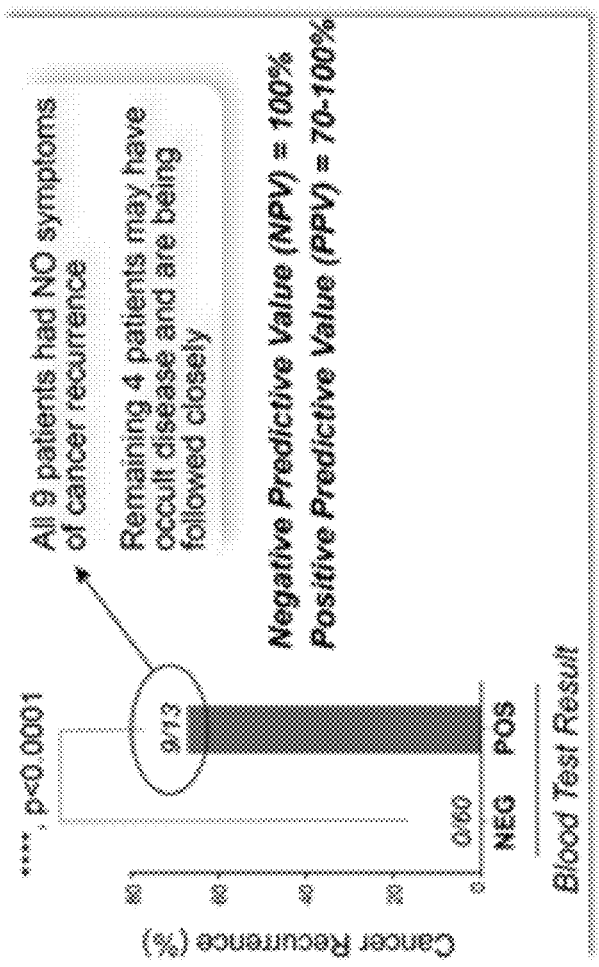
FIG. 7: The ctHPVDNA test described here was applied to a cohort of 73 patients who had completed treatment for HPV+ Oropharyngeal cancer. These patients had no evidence of disease and were clinically asymptomatic. They were monitored with the ctHPVDNA blood test at each follow up visit. 60 out of 73 patients had undetectable ctHPVDNA at all follow up visits, and none of these patients developed disease recurrence during the follow up period. In contrast, 13 out of 73 patients developed a positive ctHPVDNA blood test during the clinical follow up period. 9 out of these 13 patients have also developed clinically evident disease recurrence. The ctHPVDNA blood test was positive up to 6 months prior to identification of recurrent disease on a diagnostic radiology scan. The remaining 4 patients who have a positive blood test are being closely monitored for possible disease recurrence.

Early detection of HPV-positive cancer recurrence in healthy patients that are asymptomatic and considered disease-free using existing clinical procedures. The typical surveillance schedule after chemo-radiation therapy is clinical examinations (physical examination and fiberoptic nasopharyngolaryngoscopy) every 2 to 6 months for the first 5 years. Most head and neck oncologist also obtain PET/CT every 6 to 12 months. There are currently no available surveillance blood tests for patients with HPV-associated OPSCC. The availability of highly sensitive blood-based surveillance test would aide in early detection of cancer recurrence (prior to clinical or radiographic findings) and improve the value of cancer surveillance in this population by reducing the frequency of office visits and the use of expensive radiological imaging studies. To date 73 patients have been prospectively surveilled with HPV-associated OPSCC (FIG. 7). Blood samples were obtained with each follow-up visit regardless of clinical findings. Plasma ctHPV16DNA has become detectable in follow up after treatment in 13 patients (median copies/ml and range) of which 9 have had clinical/radiographic evidence of cancer recurrence. These patients with detectable ctHPV16DNA after treatment were asymptomatic and had radiographic examinations confirming very early, low volume cancer recurrences. An illustrative case example is presented in FIG. 8. Here, the patient had already completed curative-intent therapy and was completely asymptomatic with no evidence of disease. However, he developed a positive result for tumor-derived viral HPV DNA in the blood in June 2017. Soon thereafter, he was examined by an oncologist and determined to have no evidence of disease. Three months later, he had another follow up visit and the oncologist did not identify any evidence for disease recurrence on physical exam. However, the patient reported some neck/shoulder pain, which was believed to be musculoskeletal in nature. A neck/shoulder MRI was ordered, and on this exam—4 months after the initially positive blood test—an isolated abnormally enlarged lymph node was identified in the neck. This abnormal mass was subsequently biopsied and proven to be recurrent HPV+ oropharyngeal cancer.

There are 4 patients in the study who have detectable HPV DNA in the blood using the disclosed methods, yet have no clinical/radiographic evidence of disease and are being closely followed for recurrence. No cancer recurrences have been detected in patients with undetectable ctHPV16DNA. In summary the negative predictive value and positive predictive value of the plasma ctHPV16DNA assay in detecting cancer recurrence is 100% and 70%, respectively. These observations suggest that plasma ctHPVDNA is exquisitely specific and sensitive for the early detection of HPV-associated cancer. Application of the disclosed method as part of clinical care may improve the effectiveness and reducing the cost of cancer surveillance for patients with HPV-associated oropharyngeal cancer.

Figure 8:
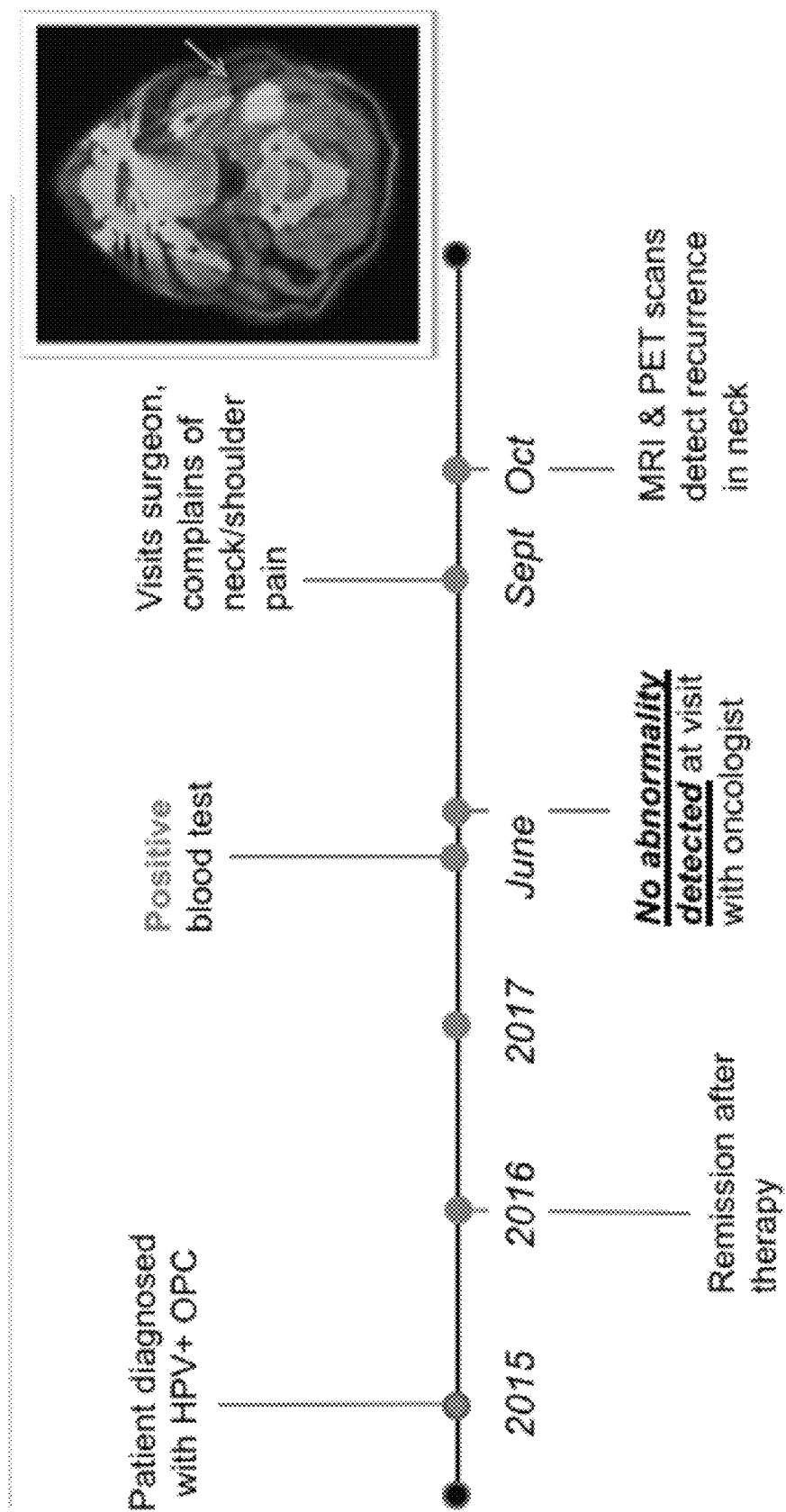
FIG. 8: Case example from the ctHPVDNA surveillance study. This patient was clinically asymptomatic and believed to be cancer-free. In June 2017 he developed a positive ctHPVDNA blood test. Soon thereafter, he was examined by an oncologist and was found to have no evidence of disease. Three months later, he was again examined by a clinician who did not identify any evidence for disease recurrence. However, the patient reported some neck/shoulder pain, which was believed to be musculoskeletal in nature. A neck/shoulder MRI was ordered, and on this exam—4 months after the blood test was positive—an isolated abnormally enlarged lymph node was identified that was subsequently biopsied and consistent with recurrent HPV+ oropharyngeal cancer.

Example 5: Plasma Circulating Tumor HPVI6DNA as a Biomarker for Treatment of HPV-Associated OPSCC The RTOG 0129 study demonstrated that exposures influence clinical risk in oropharyngeal cancer. HPV-positive patients tend to do well, and HPV-negative patients with extensive smoking history do poorly. Most studies, including RTOG 0129, also demonstrate an intermediate prognosis for HPV+ cancers that develop in heavy smokers. This is shown in FIG. 8.

Genetic biomarkers can improve clinical risk stratification. For example, as shown in FIG. 9, a subset of tumors in HPV+ non-smokers may be exceptionally sensitive to therapy, whereas, there may be smokers with HPV+ cancers that have more HPV-like biology, and others that may have more tobacco-like biology. Biomarkers may be able to identify these subgroups better than clinical parameters alone.

Plasma ctHPVDNA is detected in a majority of HPV-OPSCC patients. As such, ctHPV DNA can be a biomarker of tumor burden, and as importantly, response kinetics. Plasma circulating tumor HPV DNA can also inform decisions regarding who is appropriate for de-escalated therapy of HPV-associated OPSSC.

A digital PCR assay has been developed for HPV16 DNA that is: highly specific, in that the assay does not cross-detect HPV-18, -31, -33, or 35, and has very low background signal; linear over 5 orders of magnitude in copy number (5-50,000 copies); precise and has exceptional reproducibility; and ultra-sensitive and can detect as few as 6 copies of HPV16 with ~80% sensitivity. This is shown in FIGS. 1A and 1B. FIG. 1A shows an example readout of this assay where positive droplets indicate the presence of individual HPV16 DNA molecules, that are well separated from the negative droplets in a reaction. FIG. 1B shows the 95% confidence interval of a linear regression, demonstrating incredible linearity and precision, with assay variability only becoming an issue in the 10 target copy range. This assay can detect as few as 6 target molecules of HPV16 DNA using an assay threshold that gives no false positives.

A study population including 64 patients with biopsy-proven HPV-positive OPSCC that overexpressed p16 (IHC) and/or were HPV ISH positive. All patients received definitive chemoradiation (no induction chemo). 54 patients (84%) enrolled in a prospective CRT de-intensification trial (60 Gy IMRT+weekly Cisplatin 30 mg/m$^2$). Of these, 46 patients were clinically favorable (<T4 and ≤10 pack-years tobacco), and 18 were clinically unfavorable (T4 or >10 pack-years tobacco). No patients had N3 or M1 disease. Research bloods were collected pre-treatment, weekly during CRT, and at post-treatment clinic visits (~450 blood samples analyzed).

Figure 3A:
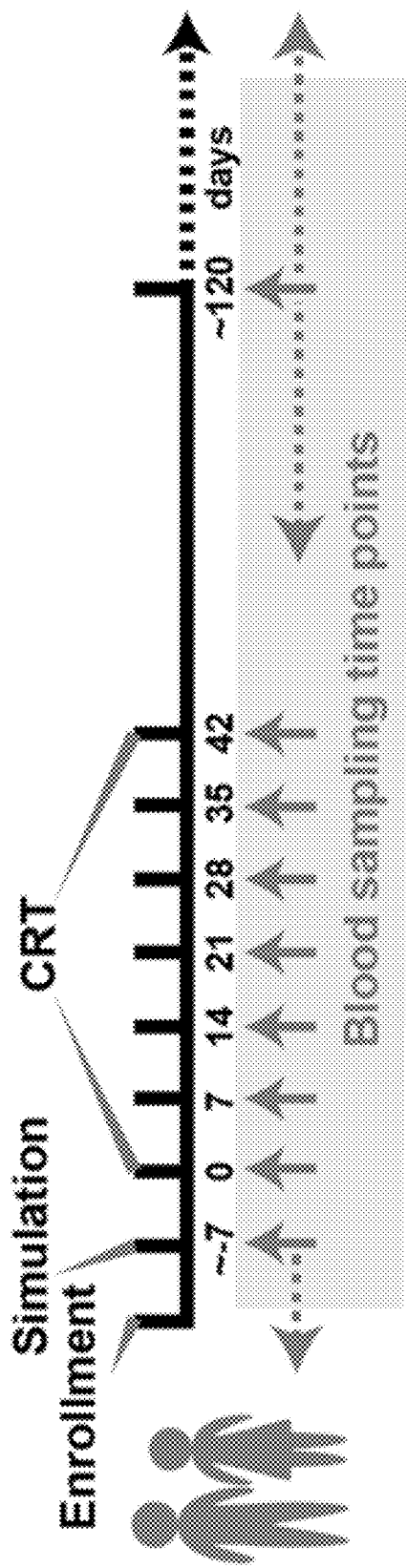
FIGS. 3A-3D.
Figure 3B:
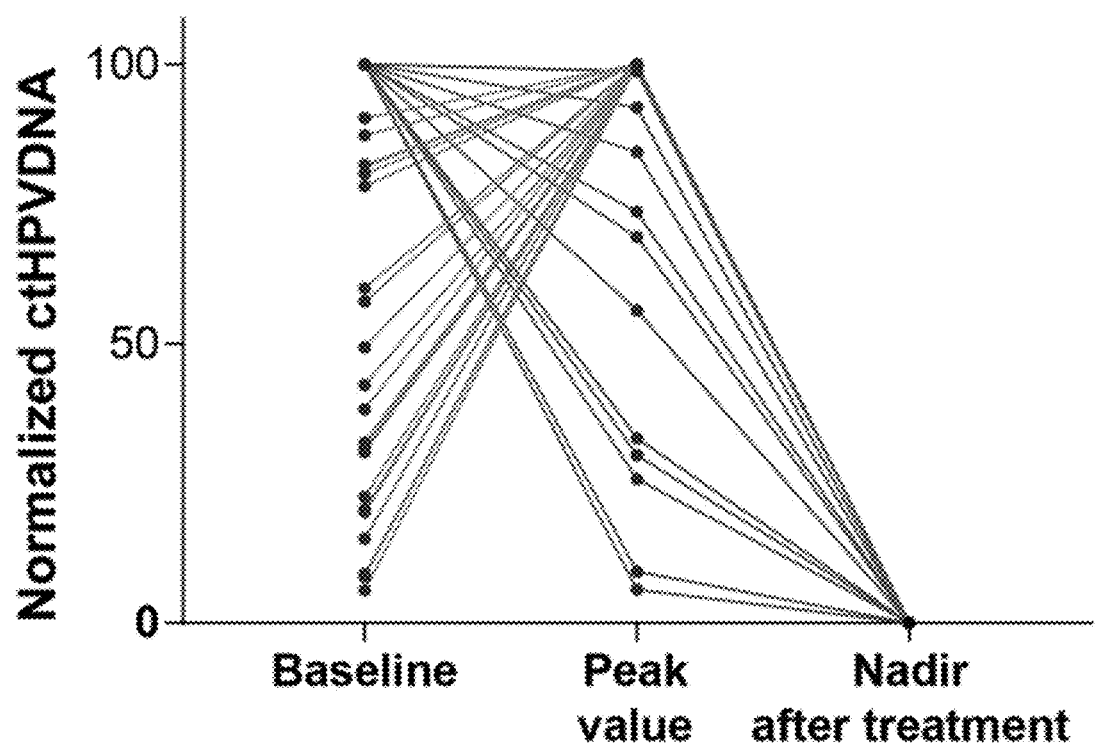

Plasma ctHPV16DNA levels were measured during chemoradiotherapy. Plasma ctHPV16DNA is responsive to CRT and in most cases is "cleared" after treatment. Its potential as a biomarker of treatment efficacy, and correlation of peak-ctHPV16DNA levels with smoking status, disease burden, and tumor HPV copy number was evaluated. This regimen is shown in FIG. 10, and normalized levels of ctHPV16DNA is depicted in FIG. 3A.

Plasma ctHPV16 DNA was detected in 77% of the patients, and FIG. 11 indicates the peak value for each patient. As shown in FIG. 11, broad range of values was observed, with as few as 10 copies per mL to as high as 30,000 copies per mL being observed. There were also 23% of patients who did not have any detectable HPV16 DNA in plasma. Furthermore, any significant correlation between the amount of HPV16 in plasma and smoking status was not seen.

Figure 3C:
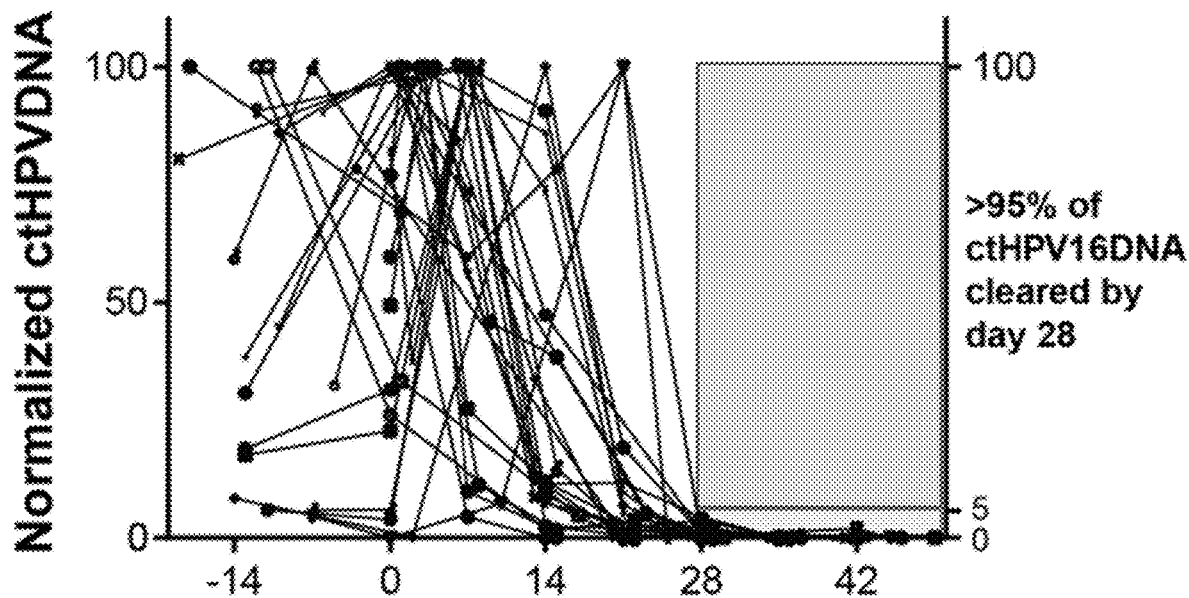
Figure 3D:
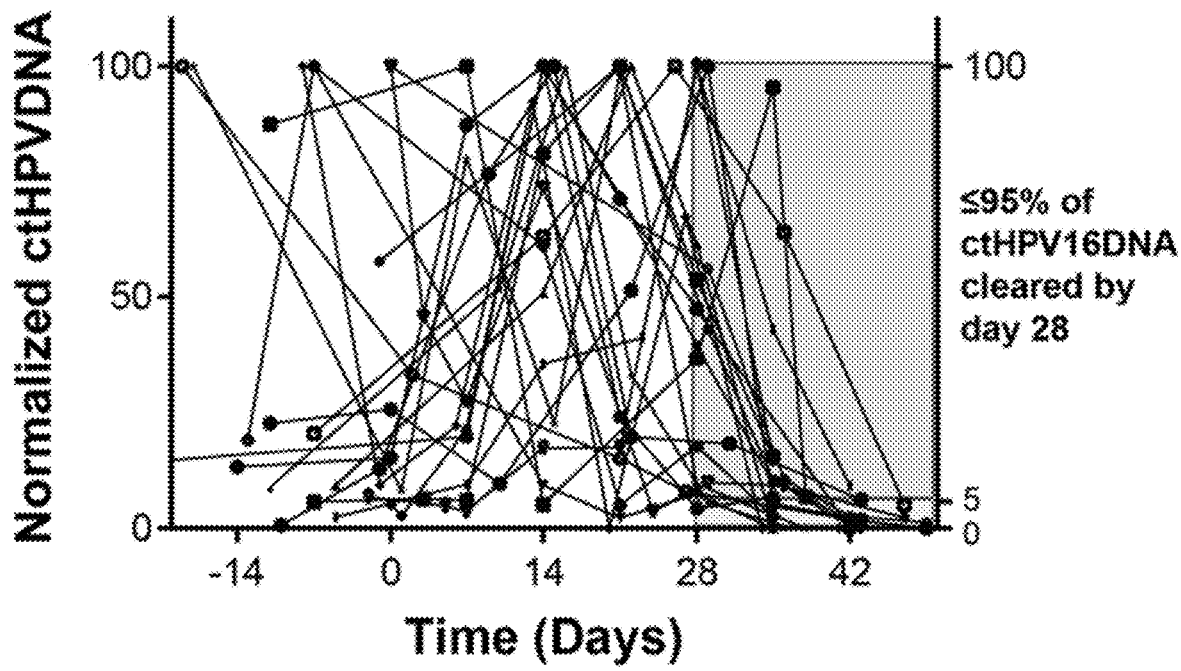
Figure 4B:
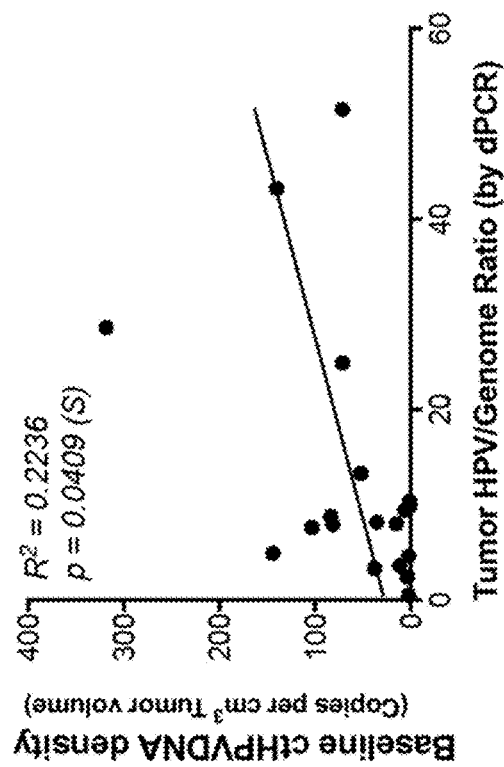
FIG. 4A-F: A subset of 20 patients with HPV+OPC had next generation sequencing (NGS) analysis of their primary tumor as well as ctHPVDNA analyses of their blood to investigate potential correlation between these assays.
Figure 4A:
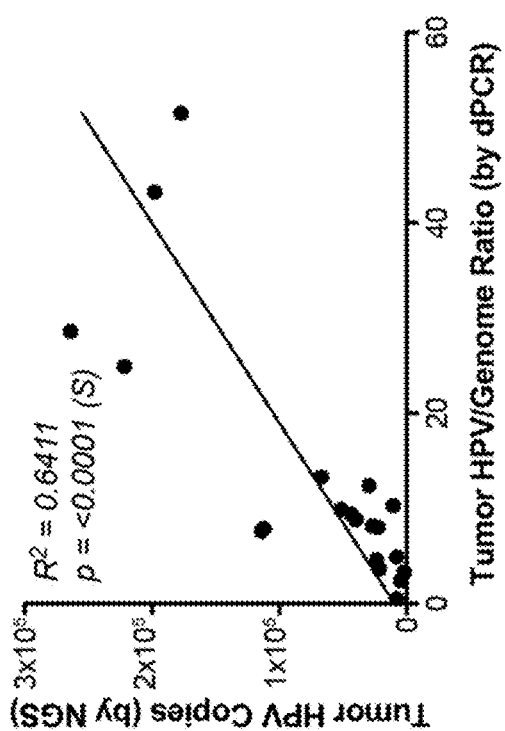
Figures 4C, 4D:
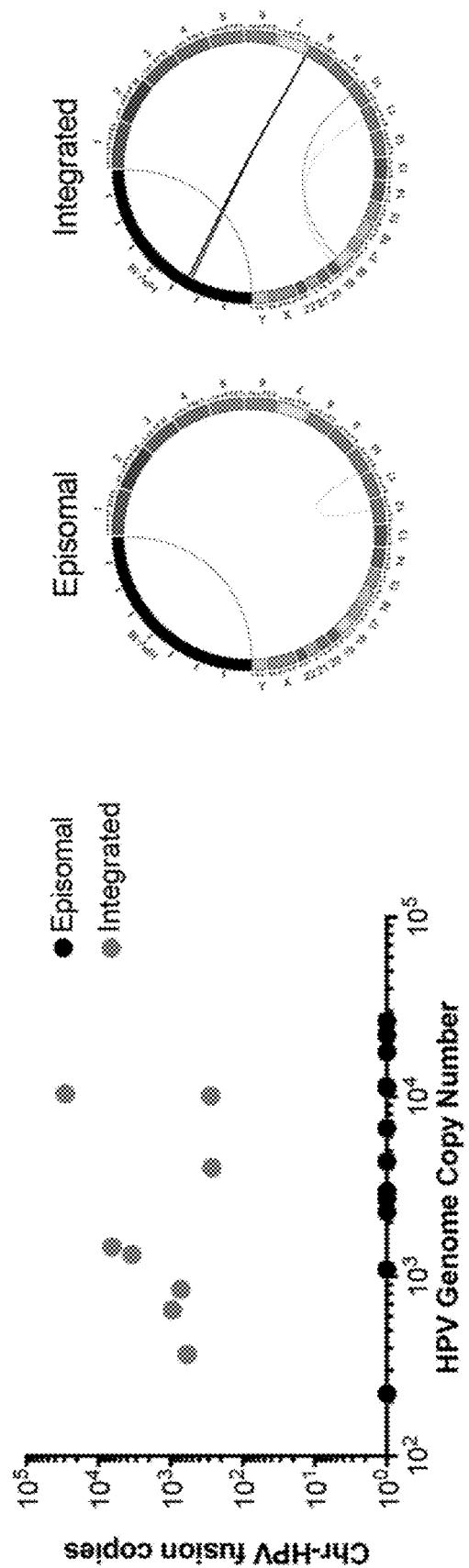
Figure 4F:
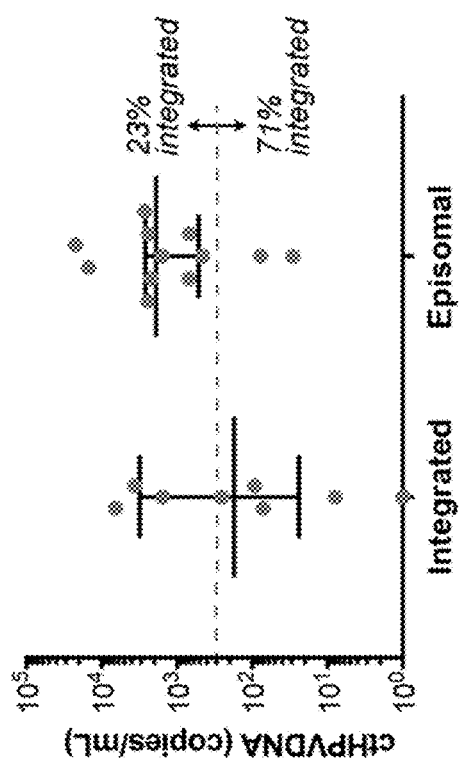
Figure 4E:
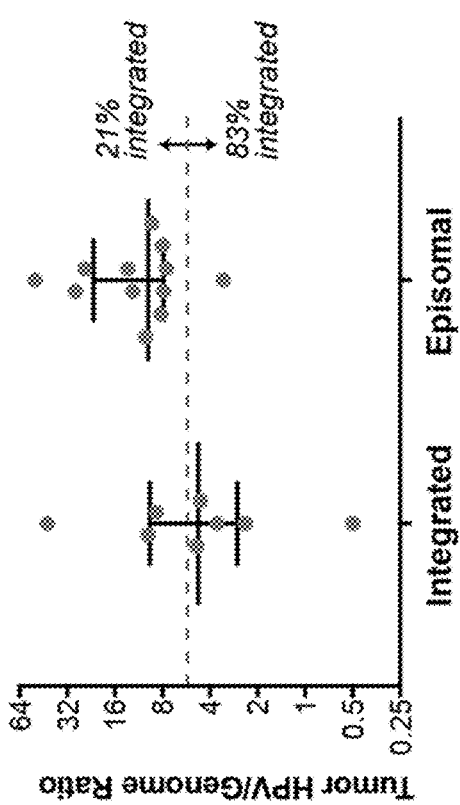

However, plasma ctHPV16 levels did not exhibit significant correlation with disease burden, as shown in FIG. 3C. Many different ways for a correlation between disease burden and peak HPV16 DNA values were looked into, one could not be found. However, by analyzing a 25 patient subset in whom tumor sequencing and plasma HPV16 DNA had been matched, a modest but statistically significant correlation between plasma circulating tumor HPV16 and copy number of HPV16 in the tumor was identified, shown in FIG. 3D. Thus, the number of HPV16 copies in plasma for a particular patient may reflect HPV copy number in their tumor, and have prognostic implications beyond disease stage and smoking history.

Attention was next turned to the HPV16 negative patients, and digital PCR assays were developed for the 4 most common alternative HPV strains. This analysis is shown in FIG. 12. Indeed among the non-heavy smokers, all of the HPV16 negative patients had detectable HPV 18/31/33 or 35 in their plasma. Among patients who were heavy smokers a significantly different pattern was observed. Slightly fewer patients were HPV16 positive. But among the HPV16 negative patients, only about ⅓rd had variant HPVs detectable, with the remainder negative for all 5 HPV strains. Perhaps even more concerning, 2 out of these four patients had a positive neck dissection post-treatment, and one patient also tested positive for a p53 mutation in the tumor. Among non-smokers no increased disease events with alternative HPV strains were observed, however, among smokers there were only 2 patients here but one of them developed regional recurrence soon after completing CRT. Thus, there seems to be an interactive effect of HPV16 negativity and smoking status.

Variable clearance kinetics among patients who were high expressers of HPV16 was also observed. As shown in FIG. 13, some patients had exponential clearance of HPV16 DNA and others had a more complex kinetic pattern with delayed clearance from plasma. This was quantified by measuring how much plasma HPV DNA was present at week 4 relative to the peak HPV value. For the top patient, this value is 0%, and for the bottom it is 39%. The median value of 5% was used to stratify patients as having either rapid clearance or delayed clearance kinetics.

Putting this all together, plasma circulating tumor HPV16 based risk groups were defined. This is depicted in FIG. 14. The favorable risk patients had abundant HPV16 and rapid clearance kinetics. All other patients had unfavorable circulating tumor HPV16 profiles either due to delayed kinetics, low copy number, due to being positive for variant HPVs, or due to undetectable HPV. For both non-smokers and smokers approximately 30% of patients had a favorable circulating tumor HPV16 profile, and 70% were unfavorable. Again noted here is the 20% subset of smokers in whom the 5 most common HPV strains were not detected.

As shown in FIG. 4, patients with a favorable circulating tumor HPV16 profile did not have any regional disease events—regardless of smoking status. However, in cases of patients having an unfavorable circulating tumor HPV profile, smoking status had a major impact. Non-heavy smokers still did well, with 90% regional disease control. However, heavy smokers or the minority presenting with T4 disease had dismal regional disease control when they also had unfavorable plasma circulating tumor HPV16 profiles.

In summary, plasma ctHPV16 DNA reveals genetic heterogeneity among HPV-associated OPSCC patients 4/18 (22%) patients with >10 pack-years tobacco or T4 disease and p16+ OPSCC were negative for HPV-16/18/31/33/35. Approximately 30% of HPV-associated OPSCC have a favorable ctHPV16 Profile (i.e., ≥200 copies/mL and rapid clearance kinetics) unfavorable ctHPV16 profiles (i.e., low/undetectable or delayed clearance) are strongly associated with regional disease failure in heavy smokers. Assessment of ctHPV16 profiles can help guide treatment intensity in non-smokers and smokers being treated for HPV-associated OPSCC.

Example 6: Application to Cancer Surveillance in a Longitudinal Clinical Study of Patients that do not Exhibit any Clinical Evidence of Cancer Following Therapy A prospective study was conducted of 73 patients who previously were diagnosed with an HPV+ malignancy but were deemed to have "no evidence of disease" after curative intent therapy. The HPV blood test was applied to these patients during a routine follow-up. None of the patients who tested negative in the HPV blood test developed a new HPV+ cancer or recurrence of the prior HPV+ cancer. In contrast, 9 out of 13 patients who tested positive in the HPV blood test were diagnosed with an HPV+ cancer.

FIG. 7 depicts results of HPV blood tests. Negative samples can be clearly distinguished from positive samples. FIG. 8 shows a case summary for a patient who tested positive according to the HPV blood test, but who exhibited no abnormality or evidence of disease at a follow-up visit with the oncologist, and who had a recurrence of disease several months after the follow-up.

A summary of the clinical results is shown in FIG. 7. These results show the predictive effectiveness of the HPV blood test. Of the 73 patients in the study, 60 tested negative according to the HPV blood test, and of which none exhibited a recurrence of disease. In contrast, of the 13 patients that tested positive according to the HPV blood test, 9 had a recurrence of disease, while the remaining 4 are being monitored closely for recurrence.

The foregoing is illustrative of the present invention, and is not to be construed as limiting thereof. The invention is defined by the following claims, with equivalents of the claims to be included therein.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of identifying a patient as having an increased likelihood of having a human papilloma virus (HPV)-associated cancer, the method comprising (a) obtaining a blood-based sample from the patient;

(b) obtaining at least two different primer/probe sets for at least two different amplicon regions within an HPV genome, wherein the primer/probe sets each include:
   a first primer/probe set configured to amplify a first region within the HPV genome to produce a first amplicon signal, and
   a second primer/probe set configured to amplify a second region within the HPV genome to produce a second amplicon signal,
   wherein the first and second amplicon regions are each less than 170 base pairs in length, and wherein the first and second regions are non-overlapping;

(c) fractionating cell-free HPV viral DNA from the sample into droplets at a concentration wherein only 0 or 1 DNA fragment is present in each droplet;

(d) amplifying cell-free HPV viral DNA in the droplets with the at least first and second primer/probe sets to produce at least the first and second amplicon signals, if present;

(e) detecting in each droplet any of the first and second amplicon signals; and (f) providing a detection signal indicating that an HPV viral DNA fractionated into the droplet is a tumor-derived HPV viral DNA only when either the first amplicon signal or the second amplicon signal, but not both, is present in the droplet;

wherein the presence of a detection signal in the sample indicates that the subject has an increased likelihood of having an HPV associated cancer.

2. The method of claim 1, wherein an HPV associated cancer has not been clinically detected in the patient.

3. The method of claim 1, wherein the patient exhibits no clinical symptoms of an HPV associated cancer.

4. The method of claim 1, wherein the first and second amplicon regions are less than 150 base pairs in length.

5. The method of claim 1, wherein amplifying cell-free HPV viral DNA comprises amplification using a polymerase chain reaction (PCR).

6. The method of claim 1, wherein the cell-free HPV viral DNA from the sample is fractionated into micro-droplets by emulsification.

7. The method of claim 6, wherein the cell-free HPV viral DNA from the sample is fractionated into micro-droplets based on size prior to performing emulsification into micro-droplets.

8. The method of claim 1, wherein the HPV associated cancer is oropharyngeal squamous cell carcinoma (OPSCC).

9. The method of claim 1, wherein the method has a 95% sensitivity and 100% specificity in identifying a patient with an HPV associated cancer.

10. A method of determining whether a patient has an increased likelihood of having a recurrence of a human papilloma virus (HPV)-associated cancer, the method comprising:
   (a) obtaining a blood-based sample from the patient, wherein the patient has been previously diagnosed with and treated for an HPV associated cancer;
   (b) obtaining at least two different primer/probe sets for at least two different amplicon regions within an HPV genome, wherein the primer/probe sets each include:
      a first primer/probe set configured to amplify a first region within the HPV genome to produce a first amplicon signal, and
      a second primer/probe set configured to amplify a second region within the HPV genome to produce a second amplicon signal,
      wherein the first and second amplicon regions are each less than 170 base pairs in length, and wherein the first and second regions are non-overlapping;
   (c) fractionating cell-free HPV viral DNA from the sample into droplets at a concentration wherein only 0 or 1 DNA fragment is present in each droplet;
   (d) amplifying cell-free HPV viral DNA in the droplets with the at least first and second primer/probe sets to produce at least the first and second amplicon signals, if present;
   (e) detecting in each droplet any of the first and second amplicon signals; and
   (f) providing a detection signal indicating that an HPV viral DNA fractionated into the droplet is a tumor-derived HPV viral DNA only when either the first amplicon signal or the second amplicon signal, but not both, is present in the droplet;
   wherein the presence of a detection signal in the sample indicates that the subject has an increased likelihood of having a recurrence of the HPV associated cancer.

11. The method of claim 10, wherein the HPV associated cancer is oropharyngeal squamous cell carcinoma (OPSCC).

12. The method of claim 10, wherein the method has a 95% sensitivity and 100% specificity in identifying a patient having an increased likelihood of having a recurrence of the HPV associated cancer.

* * * * *

SEQUENCE LISTING

```
<160> NUMBER OF SEQ ID NOS: 22

<210> SEQ ID NO 1
<211> LENGTH: 19
<212> TYPE: DNA
<213> ORGANISM: Artificial Sequence
<220> FEATURE:
<223> OTHER INFORMATION: Synthetic Construct

<400> SEQUENCE: 1
tgactctacg cttcggttg                                               19

<210> SEQ ID NO 2
<211> LENGTH: 19
<212> TYPE: DNA
<213> ORGANISM: Artificial Sequence
<220> FEATURE:
<223> OTHER INFORMATION: Synthetic Construct

<400> SEQUENCE: 2
gcccattaac aggtcttcc                                               19

<210> SEQ ID NO 3
<211> LENGTH: 30
<212> TYPE: DNA
<213> ORGANISM: Artificial Sequence
<220> FEATURE:
<223> OTHER INFORMATION: Synthetic Construct

<400> SEQUENCE: 3
cgtacaaagc acacacgtag acattcgtac                                   30

<210> SEQ ID NO 4
<211> LENGTH: 19
<212> TYPE: DNA
<213> ORGANISM: Artificial Sequence
<220> FEATURE:
<223> OTHER INFORMATION: Synthetic Construct
```

-continued

```
<400> SEQUENCE: 4
ggtttgtaac atcccaggc                                                 19

<210> SEQ ID NO 5
<211> LENGTH: 25
<212> TYPE: DNA
<213> ORGANISM: Artificial Sequence
<220> FEATURE:
<223> OTHER INFORMATION: Synthetic Construct

<400> SEQUENCE: 5
gtgtattttt taagggatc ttctt                                           25

<210> SEQ ID NO 6
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (6)..(7)
<223> OTHER INFORMATION: 2'-O-methylcytidine
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: modified_base
<222> LOCATION: (9)..(9)
<223> OTHER INFORMATION: 2'-O-methylguanosine
<220> FEATURE:
<221> NAME/KEY: misc_feature
<222> LOCATION: (9)..(9)
<223> OTHER INFORMATION: n is a, c, g, or t

<400> SEQUENCE: 6
cacctnnanc acc                                                       13

<210> SEQ ID NO 7
<211> LENGTH: 24
<212> TYPE: DNA
<213> ORGANISM: Artificial Sequence
<220> FEATURE:
<223> OTHER INFORMATION: Synthetic Construct

<400> SEQUENCE: 7
atctgtacag catgaagtgc aaga                                           24

<210> SEQ ID NO 8
<211> LENGTH: 19
<212> TYPE: DNA
<213> ORGANISM: Artificial Sequence
<220> FEATURE:
<223> OTHER INFORMATION: Synthetic Construct

<400> SEQUENCE: 8
ctagtgggcg catgtaggc                                                 19

<210> SEQ ID NO 9
<211> LENGTH: 11
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (2)..(2)
<223> OTHER INFORMATION: 2'-O-methylcytidine
```

```
<220> FEATURE:
<221> NAME/KEY: misc_feature
<222> LOCATION: (2)..(4)
<223> OTHER INFORMATION: n is a, c, g, or t
<220> FEATURE:
<221> NAME/KEY: modified_base
<222> LOCATION: (3)..(3)
<223> OTHER INFORMATION: 2'-O-methylthymidine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (6)..(6)
<223> OTHER INFORMATION: 2'-O-methylguanosine
<220> FEATURE:
<221> NAME/KEY: misc_feature
<222> LOCATION: (6)..(8)
<223> OTHER INFORMATION: n is a, c, g, or t
<220> FEATURE:
<221> NAME/KEY: modified_base
<222> LOCATION: (7)..(7)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methylcytidine

<400> SEQUENCE: 9
tnnntnnnct g                                                          11

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
tgaagccaga attgagctag                                                 20

<210> SEQ ID NO 11
<211> LENGTH: 18
<212> TYPE: DNA
<213> ORGANISM: Artificial Sequence
<220> FEATURE:
<223> OTHER INFORMATION: Synthetic Construct

<400> SEQUENCE: 11
aggacagggt gttcagaa                                                   18

<210> SEQ ID NO 12
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (3)..(3)
<223> OTHER INFORMATION: 2'-O-methylguanosine
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: modified_base
<222> LOCATION: (5)..(5)
<223> OTHER INFORMATION: 2'-O-methylcytidine
```

```
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: modified_base
<222> LOCATION: (6)..(6)
<223> OTHER INFORMATION: 2'-O-methylguanosine
<220> FEATURE:
<221> NAME/KEY: modified_base
<222> LOCATION: (9)..(9)
<223> OTHER INFORMATION: 2'-O-methylcytidine
<220> FEATURE:
<221> NAME/KEY: misc_feature
<222> LOCATION: (9)..(9)
<223> OTHER INFORMATION: n is a, c, g, or t

<400> SEQUENCE: 12
canannacnt tcg                                                           13

<210> SEQ ID NO 13
<211> LENGTH: 21
<212> TYPE: DNA
<213> ORGANISM: Artificial Sequence
<220> FEATURE:
<223> OTHER INFORMATION: Synthetic Construct

<400> SEQUENCE: 13
agcacacaag tagatattcg c                                                  21

<210> SEQ ID NO 14
<211> LENGTH: 19
<212> TYPE: DNA
<213> ORGANISM: Artificial Sequence
<220> FEATURE:
<223> OTHER INFORMATION: Synthetic Construct

<400> SEQUENCE: 14
tagtagaaca gttggggca                                                     19

<210> SEQ ID NO 15
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (4)..(4)
<223> OTHER INFORMATION: 2'-O-methylcytidine
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: modified_base
<222> LOCATION: (5)..(5)
<223> OTHER INFORMATION: 2'-O-methyladenosine
<220> FEATURE:
<221> NAME/KEY: modified_base
<222> LOCATION: (7)..(7)
<223> OTHER INFORMATION: 2'-O-methylcytidine
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: modified_base
<222> LOCATION: (9)..(9)
<223> OTHER INFORMATION: 2'-O-methylcytidine
```

<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: modified_base
<222> LOCATION: (10)..(10)
<223> OTHER INFORMATION: 2'-O-methylthymidine
<220> FEATURE:
<221> NAME/KEY: modified_base
<222> LOCATION: (13)..(13)
<223> OTHER INFORMATION: 2'-O-methylcytidine
<220> FEATURE:
<221> NAME/KEY: misc_feature
<222> LOCATION: (13)..(13)
<223> OTHER INFORMATION: n is a, c, g, or t

<400> SEQUENCE: 15
taanngntnn tgn                                                          13

<210> SEQ ID NO 16
<211> LENGTH: 22
<212> TYPE: DNA
<213> ORGANISM: Artificial Sequence
<220> FEATURE:
<223> OTHER INFORMATION: Synthetic Construct

<400> SEQUENCE: 16
taacaccaca gttcgtttat gt                                                22

<210> SEQ ID NO 17
<211> LENGTH: 21
<212> TYPE: DNA
<213> ORGANISM: Artificial Sequence
<220> FEATURE:
<223> OTHER INFORMATION: Synthetic Construct

<400> SEQUENCE: 17
acaatattca ctgtgcccat a                                                 21

<210> SEQ ID NO 18
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: modified_base
<222> LOCATION: (5)..(5)
<223> OTHER INFORMATION: 2'-O-methylcytidine
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: modified_base
<222> LOCATION: (6)..(6)
<223> OTHER INFORMATION: 2'-O-methylthymidine
<220> FEATURE:
<221> NAME/KEY: modified_base
<222> LOCATION: (8)..(8)
<223> OTHER INFORMATION: 2'-O-methylcytidine

```
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: modified_base
<222> LOCATION: (10)..(11)
<223> OTHER INFORMATION: 2'-O-methyladenosine
<220> FEATURE:
<221> NAME/KEY: misc_feature
<222> LOCATION: (10)..(11)
<223> OTHER INFORMATION: n is a, c, g, or t

<400> SEQUENCE: 18
tgncnnangn ncc                                                      13

<210> SEQ ID NO 19
<211> LENGTH: 17
<212> TYPE: DNA
<213> ORGANISM: Artificial Sequence
<220> FEATURE:
<223> OTHER INFORMATION: Synthetic Construct

<400> SEQUENCE: 19
tgaggcgaca ctacgtc                                                  17

<210> SEQ ID NO 20
<211> LENGTH: 23
<212> TYPE: DNA
<213> ORGANISM: Artificial Sequence
<220> FEATURE:
<223> OTHER INFORMATION: Synthetic Construct

<400> SEQUENCE: 20
gtgcccatta ataaatcttc caa                                           23

<210> SEQ ID NO 21
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: modified_base
<222> LOCATION: (5)..(5)
<223> OTHER INFORMATION: 2'-O-methylcytidine
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (9)..(9)
<223> OTHER INFORMATION: 2'-O-methylcytidine
<220> FEATURE:
<221> NAME/KEY: misc_feature
<222> LOCATION: (9)..(10)
<223> OTHER INFORMATION: n is a, c, g, or t
```

```
<220> FEATURE:
<221> NAME/KEY: modified_base
<222> LOCATION: (10)..(10)
<223> OTHER INFORMATION: 2'-O-methyladenosine

<400> SEQUENCE: 21
agngnncann cat                                                        13

<210> SEQ ID NO 22
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (3)..(3)
<223> OTHER INFORMATION: 2'-O-methylcytidine
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: modified_base
<222> LOCATION: (5)..(5)
<223> OTHER INFORMATION: 2'-O-methylcytidine
<220> FEATURE:
<221> NAME/KEY: misc_feature
<222> LOCATION: (5)..(7)
<223> OTHER INFORMATION: n is a, c, g, or t
<220> FEATURE:
<221> NAME/KEY: modified_base
<222> LOCATION: (6)..(6)
<223> OTHER INFORMATION: 2'-O-methylguanosine
<220> FEATURE:
<221> NAME/KEY: modified_base
<222> LOCATION: (9)..(9)
<223> OTHER INFORMATION: 2'-O-methylguanosine
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: modified_base
<222> LOCATION: (10)..(10)
<223> OTHER INFORMATION: 2'-O-methyladenosine

<400> SEQUENCE: 22
canannnann cat                                                        13
```